(12) United States Patent
Donadio et al.

(10) Patent No.: US 8,609,367 B2
(45) Date of Patent: Dec. 17, 2013

(54) GENES AND PROTEINS FOR THE BIOSYNTHESIS OF THE LANTIBIOTIC 107891

(75) Inventors: Stefano Donadio, Malnate, VA (US); Margherita Sosio, Solaro (IT); Stefania Serina, Milan (IT); Davide Mercorillo, Lazzate (IT)

(73) Assignee: Sentinella Pharmaceuticals, Inc., Princeton, NJ (US)

( * ) Notice: Subject to any disclaimer, the term of this patent is extended or adjusted under 35 U.S.C. 154(b) by 258 days.

(21) Appl. No.: 12/671,845

(22) PCT Filed: Aug. 3, 2007

(86) PCT No.: PCT/IB2007/002270
§ 371 (c)(1),
(2), (4) Date: Sep. 29, 2011

(87) PCT Pub. No.: WO2009/019524
PCT Pub. Date: Feb. 12, 2009

(65) Prior Publication Data
US 2012/0015418 A1    Jan. 19, 2012

(51) Int. Cl.
*C12P 1/00* (2006.01)
*C12N 1/20* (2006.01)
*C12N 15/00* (2006.01)
*C07H 21/04* (2006.01)

(52) U.S. Cl.
USPC ............ 435/41; 435/252.3; 435/252.33; 435/252.31; 435/252.35; 435/320.1; 536/23.2

(58) Field of Classification Search
None
See application file for complete search history.

(56) References Cited

U.S. PATENT DOCUMENTS

2004/0101963 A1  5/2004 Bibb

FOREIGN PATENT DOCUMENTS

WO      03076898 A2    9/2003
WO    2005014628 A1    2/2005

OTHER PUBLICATIONS

Siezen R. J. et al.: "Comparison of Lantibiotic Gene Clusters and Encoded Proteins" Antoine Van Leewnhoek, Bordrecht, NL, vol. 2, No. 69, Feb. 1996, pp. 171-184.
Widdick D. A. et al.: "Cloning and engineering of th cinnamycin biosynthetic gene cluster from *Streptomyces cinnamonous* cinnamoneus DSM 40005" Proceedings of the National Academy of Sciences of USA, National Academy of Science, Washington, DC, US, vol. 1000, No. 7, Apr. 1, 2003, pp. 436-4321.
McAuliffe Olivia et al.: "Lantibiotics: Structure, Biosynthesis and Mode of Action" FEMS Microbiology Reviews, Elsevier, Amsterdam, NL, vol. 25, No. 3, May 2001, pp. 285-308.
Hillman J. D. et al.: "Genetic and Biochemical Analysis of Mutacin 1140, a Lantibiotic and *Streptococcus* Mutans" Infection and Immunity, American Society for Microbiology, Washington, DC, US, vol. 66, No. 6, Jun. 1998, pp. 2743-2749.
Gillor O. et al.: "Genetically Engineered Bacteriocins and Their Potential as the Next Generation of Antimicrobials" Curren Pharmaceutical Design, Bentham Science Publishers, Schiphol, NL vol. 11, No. 8, Mar. 2005, pp. 1067-1075.
Volokhan O. et al.: "An Unexpected Role for the Putative 4'-Phosphopamtetheinyl Transterase-Encoding Gene nsyF in the Regulation if Nystatin Biosynthesis in Streptomyces Noursei ATCC 11455" FEMS Microbiology Letters, Amsterdam, NL, vol. 249, No. 1, Aug. 1, 2005, pp. 57-64.
Klein C. et al.: "Analysis of Genes Involved in Biosynthesis of the Lantibiotic Subtilin" Applied and Environmental Microbiology, vol. 58, No. 1, 1992, pp. 132-142.
Rendulic Snjezana et al.: "A Predator Unmasked: Life Cycle of Bdllovibrio Bacterovorus From a Genomic Perspective" Science (Washington DC), vol. 303, No. 5658, Jan. 30, 2004, pp. 689-692.
International Search Report from International Application No. PCT/IB2007/002270.

*Primary Examiner* — Nashaat Nashed
(74) *Attorney, Agent, or Firm* — Morgan Lewis & Bockius LLP

(57) ABSTRACT

The invention relates to the field of lantibiotics, and more specifically to the isolation of nucleic acid molecules that code for the enzymes required for the biosynthetic pathway of the lantibiotic 107891 and the homologues thereof.

10 Claims, 4 Drawing Sheets

TABLE I

| mlb cluster mlb ORF | size (aa) | function[b] | GeneBank[a] Entry[c] | Probability[d] | Function, Source, function[e] |
|---|---|---|---|---|---|
| ORF1 | 300 | ABC transport | ZP_00568009 | 4e-77 | ABC transporter Frankia sp. EAN1pec |
| ORF2 | 414 | monoxygenase | P63707 | 1.5e-27 | Putative cytochrome P450, Mycobacterium tuberculosis |
| ORF3 | 260 | Transcriptional response regulator | YP_075969 | 3e-04 | two-component response regulator Symbiobacterium thermophilum |
| ORF4 | 221 | unknown | YP_001158279 | 5e-9 | Hypotetical protein Strop 1435 Salinispora tropica CNB-440 |
| ORF5 | 220 | transcriptional regulator | P37978 | 1.6e-10 | RNA polymerase sigma factor, Ralstonia metallidurans |
| ORF6 | 57 | 107891 prepropeptide | N.A. | N.A.[f] | N.A.[f] |
| ORF7 | 1115 | dehydratase | AAX37279 | 1e-130 | lantibiotic dehydratase, S.noursei ATCC11455 |
| ORF8 | 475 | Thioether bridge formation | AAA22777 | 1e-53 | SpaC, B.subtilis |
| ORF9 | 215 | oxidative decarboxylation of the C- terminal cysteine residue | Q9RC23 | 4.4e-18 | Mersacidin decarboxylase, Bacillus sp. |
| ORF10 | 316 | ABC transporter | CAD60523 | 5e-53 | CinT, S.cinnamoneus |
| ORF11 | 242 | transport system | YP_431128 | 2e-33 | ABC transporter membrane protein, Moorella thermoacetica ATCC 39073 |
| ORF12 | 211 | unknown | CAJ88585 | 9e-9 | hypothetical protein, Streptomyces ambofaciens ATCC23877 |
| ORF13 | 249 | ABC transporter | CAJ67308.1| | 3e-13 | ABC transporter, permease protein, Clostridium difficile 630 |
| ORF14 | 236 | ABC transporter | AAU21918 | 1e-49 | ABC transporter SpaF, Bacillus licheniformis ATCC 14580 |
| ORF15 | 541 | Trp halogenase | CAE79281 | 6e-107 | tryptophan halogenase, Bdellovibrio bacteriovorus HD100 |
| ORF16 | 178 | Flavin reductase | BAD38877 | 6e-34 | flavin reductase, Streptomyces carzinostaticus |
| ORF17 | 430 | Transport system | AAK81829 | 5e-95 | integral membrane ion antiporter, S.lavendulae |

[a] When no orthologs are present in other lantibiotic gene clusters, the results on Blast or Fasta searches in GeneBank/UniProt are reported
[b] function of the mlb ORFs established from the structure of 107891 or proposed on the basis of the combined results from the presence in other lantibiotic clusters and Blast or Fasta searches in GeneBank
[c] Accession number of the GeneBank/UniProt entry with the highest score
[d] Probability score obtained from Blast or Fasta searches
[e] Organism and proposed function of the GeneBank/UniProt entry from the previous column.
[f] N.A., not applicable

Figure 4

GENES AND PROTEINS FOR THE BIOSYNTHESIS OF THE LANTIBIOTIC 107891

STATEMENT OF RELATED APPLICATIONS

This application is a U.S. National Stage Patent Application, under 35 U.S.C. §371, of International Application No. PCT/IB2007/002270, filed Aug. 3, 2007, which is incorporated herein by reference in its entirety.

SUMMARY

The present invention relates to the field of lantibiotics, and more specifically to the isolation of nucleic acid molecules that code for the enzymes required for the biosynthetic pathway of the lantibiotic 107891 and the homologues thereof. Disclosed are the functions of the gene products involved in 107891 production. The present invention provides novel biosynthetic genes necessary for 107891 production, the encoded polypeptides, the recombinant vectors comprising the nucleic acid sequences that encode said polypeptides, the host cells transformed with said vectors and methods for producing lantibiotics using said transformed host cells, including methods for producing 107891, a precursor thereof, a derivative thereof or a modified lantibiotic different from 107891 or a precursor thereof.

BACKGROUND OF THE INVENTION

The continuous increase of pathogenic bacteria resistant to the existing antibiotics is a health global concern, and so there is a pressing need to discover and develop new compound that are active against resistant bacteria. This has led to renewed interest in natural products which have been in the past a rich source of antibiotics such as penicillins, macrolides and glycopeptides. Attractive candidates are also antimicrobial peptides and among them those designated as lantibiotics, i.e. lanthionine-containing antibiotic. Lantibiotics form a particular group within the antimicrobial peptides and are distinguished by several features such as primary and spatial structure characteristics, unique biosynthetic pathways and peptide modification reactions and potent antibacterial activity. These are a group of peptide-derived antimicrobial compounds secreted by Gram-positive bacteria and primarily act on Gram-positive bacteria. Lantibiotics are ribosomally synthesised as prepropeptides which are posttranslationally modified to their biologically active forms. The prepeptide consists of an N-terminal leader sequence, that does not undergo any post-translational modification and is cleaved off during or after secretion from the cell, and a C-terminal region (the propeptide), which is post-translationally modified. Lantibiotics are produced by different bacteria: the common feature of these compounds is the presence of one or more lanthionine residues, which consist of two alanine residues covalently cross-linked by a thioether linkage The thioether brigde is formed when a cysteine residue reacts with a dehydroalanine or dehydrobutyrine moiety to form a lanthionine or methyllantionine residue, respectively. The dehydroamino acid residues are in turn formed by dehydration of serine and threonine, respectively. Based on their structural and functional properties, lantibiotics are usually divided in two groups, type-A and type-B. Type-A lantibiotics are elongated, cationic peptides varying in length from 20 to 34 amino acids residues: raisin, subtilin, epidermin and Pep5 are members of this group. Type-B are globular peptides with a net negative charge: examples of this group of lantibiotics are mersacidin, cinnamycin, lacticin 481 and actagardine. These structural differences reflect on the mechanism of action. Type-A compounds exert their antimicrobial activity by blocking cell wall biosynthesis and by forming pores in the cellular membranes, through a mechanism that may or may not be aided by prior docking on the cellular target lipid II. Type-B lantibiotics also exert their antimicrobial activity by inhibiting peptidoglycan biosynthesis, but these compounds do not form pores once bound to lipid II.

Lantibiotics have been shown to have efficacy and utility as food additives and antibacterial agents. Nisin, the most studied lantibiotic, is produced by *Lactococcus lactis* and is active at low concentrations (low nanomolar MICs) against many Gram-positive bacteria including drug resistant strains and the food-borne pathogens *Clostridium botulinum* and *Listeria monocytogenes*. It has been extensively used as a food preservative without substantial development of bacterial resistance. Other lantibiotics show interesting biological activities: for example, epidermin shows high potency against *Propionibacterium acnes*; cinnamycin and duramycin inhibit phospholipase $A_2$ and angiotensin converting enzyme, providing potential applications as anti-inflammatory agents and for blood pressure regulation, respectively; and mersacidin inhibits many Gram-positive bacteria, including methicillin-resistant *Staphylococcus aureus* (MRSA).

The genes responsible for the biosynthesis of lantibiotics are organized in clusters designated by the locus symbol lan, with a more specific genotypic designation for each lantibiotic (e.g., nis for nisin, gdin for gallidermin, cin for cinnamycin). Many lan genes have been sequenced demonstrating a high level of similarity in gene organization. Each cluster includes: the structural gene lanA encoding the prepeptide; and the gene(s) required for the dehydration of Ser and Thr residues in the propeptide portion of LanA and for the thioether formation. For Type-A lantibiotics, LanB carries out the dehydration reactions and LanC is devoted to thioether bridging, whereas in Type-B lantibiotics a single LanM enzyme catalyzes both reactions. Additional genes are usually present in lantibiotic clusters: lanT encodes the ABC transporter for secretion of the lantibiotic, often in combination with a second transport system, encoded by the lanEFG genes; lanP encodes the processing protease, but some clusters lack such a gene which may be part of lanT or its function may be provided by a cellular protease; and lanI encodes a protein involved in self-protection; and lanKR are responsible for regulating expression of the lan genes.

There exists the potential and the utility to obtain improved lantibiotics by manipulation of occurring natural compounds. However, lantibiotics are structurally complex peptides and their accessibility to chemistry is limited to a few positions in the molecule. One of the major limitations for chemistry is to change the type or order of amino acids present in the peptide backbone. In light of the above, it would be desirable to have genes and enzymes useful for redirecting these steps in lantibiotic formation, in order to obtain derivatives that are hard or impossible to make by chemical means. General methods for the design of novel lantibiotic derivatives directly by fermentation processes with precisely engineered strains would thus be highly desirable.

In fact unusual aminoacids in lantibiotics solely contribute to their biological activity and also enhance their structural stability. Enzymes involved in lantibiotic biosynthesis represent a high potential for peptide engineering by introducing unusual aminoacids into desired peptides.

The lantibiotic 107891 shows antibacterial activity against Gram-positive bacteria including methycillin- and vancomycin-resistant strains but shows limited activity against Gramnegative bacteria (for examples, some *Moraxella, Neisseria* and *Haemophilus* spp.). 107891 was isolated from fermentation of *Microbispora* sp. PTA-5024 (WO 2005/04628 A1). It consists of a complex of closely related factors A1 and A2, whose structure can be reconducted to a peptide skeleton, 24 amino acids long, containing lanthionine and methyllanthionine as constituents. In addition, a chlorine atom and one or two —OH residues are present on the molecule. The structure of the components of the 107891 complex is represented by the formula 1 of FIG. 3, where R represents [OH] with the factors $A_1(R$=$OH)$, factor $A_2$ $(R$=$—(OH)_2)$. 107891 appears to combine elements of Type-A and -B lantibiotics: rings A and B in 107891 are highly related to the equivalent rings in Type-A compounds; however, as in Type-B lantibiotics, 107891 is rather globular, it lacks a flexible C-terminal tails and is devoid of charged amino acid residues. Consequently, it cannot be predicted whether the Zan cluster devoted to 107891 formation would encode a single LanM enzyme or separate LanB and LanC proteins. Furthermore, there are no precedent for chlorine-containing lantibiotics, thus the genes responsible for this post-translational modification cannot be predicted from available data.

The design of industrial processes for antibiotic production has been relatively successful, resulting in large size fermentations with antibiotic titers reaching levels of several grams per liter. This has been achieved largely by following empirical, trial and error approaches, and lacks a rational basis. Development of new processes and improvement of current technology thus remains time consuming and may result in bacterial cultures that are unstable, perform inconsistently and accumulate unwanted by-products. In recent years, rational methods have been applied successfully to increase the level of antibiotic produced by *Streptomyces* spp., which have often involved the manipulation of key regulatory elements present within the gene cluster of interest or the overexpression of rate-limiting steps in the pathway. Therefore, the genes encoding such cluster-associated regulators or limiting steps in the synthesis can be effective tools for yield improvement. However, the cluster-associated regulators so far identified in actinomycetes belong to several different protein families. Even within one family, there is considerable variation in sequence identity. Therefore, the existence, nature, number and sequence of cluster-associated regulators cannot be predicted by comparison to other cluster, even those specifying a related antibiotic. As an example, the tylosin gene cluster encodes four distinct regulators, while none has been found in the cluster specifying the related macrolide antibiotic erythromycin. Similarly, the nature and reason for a rate-limiting step in a biosynthetic pathway cannot be established a priori.

Therefore, tools for increasing the 107891 yield would be highly desirable. However, there are no examples of clusters from other members of the genus *Microbispora*. Therefore, the mechanism(s) cannot be predicted through which the producer strain protects itself from the action of 107891, governs the expression of the other lan genes, or coordinates expression of lan genes with its other cellular processes. Information about these will be very be useful for optimizing the production process.

DESCRIPTION OF THE INVENTION

The present invention provides a set of isolated polynucleotide molecules required for the biosynthesis of the lantibiotic 107891 in microorganisms.

So, according to one of its aspect, the present invention relates to polynucleotide molecules which are selected from the contiguous DNA sequence (SEQ ID NO: 1), which represents the mlb gene cluster as isolated from *Microbispora* sp. PTA-5024 and consists of 17 ORFs encoding the polypeptides required for 107891 formation.

The amino acid sequences of the polypeptide encoded by said 17 ORFs are provided in SEQ ID NOS: 2 to 18.

The present invention also provides an isolated nucleic acid comprising a nucleotide sequence selected from the group consisting of:
a) the mlb gene cluster encoding the polypeptides required for the synthesis of 107891 and homologues thereof (SEQ ID NO: 1);
b) a nucleotide sequence encoding the same polypeptides encoded by the mlb gene cluster (SEQ ID NO. 1), other than the nucleotide sequence of the mlb gene cluster itself;
c) any nucleotide sequence of mlb ORFs 1 to 17, encoding the polypeptides encoded by SEQ ID NOS: 2 to 18;
d) a nucleotide sequence encoding the same polypeptide encoded by any of mlb ORFs 1 to 17 (SEQ ID NOS: 2 to 18), other than the nucleotide sequence of said ORF.

A further subject matter of this invention is to provide an isolated nucleic acid comprising a nucleotide sequence selected from the group consisting of
e) a nucleotide sequence encoding a polypeptide that is, over its full length, at least 65%, preferably 86%, more preferably 90%, most preferably 95% or more, identical in amino acid sequence to a polypeptide encoded by any of mlb ORFs 1 to 17 (SEQ ID NOS: 2 to 18).

In one embodiment the isolated nucleic acids of this invention comprises an ORF selected from ORFs 1 to 17 (SEQ ID NOS: 2 to 18), which encodes a polypeptide required for the synthesis of the prepropetide of 107891.

In another embodiment, the nucleic acid comprises an ORF selected from ORFs 1 to 17 (SEQ ID NOS: 2 to 18), which encodes the polypeptide required for the synthesis of the 107891 dehydratase enzyme. In yet another embodiment, the nucleic acid comprises an ORF selected from ORFs 1 to 17 (SEQ ID NOS: 2 to 18), which encodes the polypeptide required for the synthesis of the lanthionine and methyllanthionine residues of 107891.

According to another embodiment, in a nucleic acid of this invention, an ORF selected from ORFs 1 to 17 (SEQ ID NOS: 2 to 18) is provided, which encodes a polypeptide required for the chlorination of the triptophan residue of amino acid 4 of 107891.

In yet another embodiment, nucleic acid comprising an ORF selected from ORFs 1 to 17 (SEQ ID NOS: 2 to 18) is provided, which encodes a polypeptide required for the hydroxylation of the proline residue of aminoacid 14 of 107891.

In yet another embodiment, nucleic acid comprising an ORF selected from ORFs 1 to 17 (SEQ ID NOS: 2 to 18) is provided, which encodes a flavoprotein required for the oxidative decarboxylation that yields the S-[(Z)-2-aminovinyl]-(3S)-3-methyl-D-cysteine (AviMeCys) residues present at positions 21 and 24 of 107891.

According to another embodiment, in the nucleic acid of this invention, an ORF selected from ORFs 1 to 17 (SEQ ID NOS: 2 to 18) is provided which encodes the polypeptide required for the reduction of the flavoprotein.

According to yet another embodiment, nucleic acids are provided which comprise combinations of ORFs selected from ORFs 1 to 17 (SEQ ID NOS: 2 to 18), encoding polypeptides required for the export of and resistance to 107891.

In yet another embodiment, nucleic acids are provided which comprise combinations of ORFs selected from ORFs 1 to 17 (SEQ ID NOS: 2 to 18), encoding polypeptides required for regulating the expression of the m/b gene cluster.

Those skilled in the art understand that the present invention, having provided the nucleotide sequences encoding polypeptides of the 107891 biosynthetic pathway, also provides nucleotides encoding fragments derived from such polypeptides. According to the invention, those skilled in the art understand that, since the genetic code is degenerate, the same polypeptides encoded by SEQ ID NOS: 2 to 18 can be encoded by natural or artificial variants of ORFs 1 to 17, i.e. by nucleotide sequences other than the genomic nucleotide sequences specified by ORFs 1 to 17 but which encode the same polypeptides.

Furthermore, it is also understood that naturally occurring or artificially manufactured variants can occur of the polypeptides encoded by SEQ ID NOS: 2 to 18, said variants having the same function(s) as the above mentioned original polypeptides but containing addition, deletion or substitution of amino acid not essential for folding or catalytic function, or conservative substitution of essential amino acids.

Those skilled in the art understand also that, having provided the nucleotide sequence of the entire cluster required for 107891 biosynthesis, the present invention also provides nucleotide sequences required for the expression of the genes present in said cluster. Such regulatory sequences include but are not limited to promoter and enhancer sequences, antisense sequences, transcription terminator and antiterminator sequences. These sequences are useful for regulating the expression of the genes present in the mlb gene cluster. Cells carrying said nucleotide sequences, alone or fused to other nucleotide sequences, fall also within the scope of the present invention.

In one aspect, the present invention provides isolated nucleic acids comprising nucleotide sequences encoding the ORF6 polypeptide (SEQ ID NO: 7), or naturally occurring variants or derivatives of said polypeptide, encoding the pre-propeptide of 107891.

In another aspect, the present invention provides nucleic acids comprising nucleotide sequences encoding the ORF7 polypeptide (SEQ ID NO: 8), or naturally occurring variants or derivatives of said polypeptide, useful for the dehydratation of serine and threonine residues in the lantibiotic precursor.

In yet another aspect, the present invention provides a nucleic acid comprising nucleotide sequences encoding the ORF8 polypeptide (SEQ ID NO: 9), or naturally occurring variants or derivatives of said polypeptide, useful for lanthionine and methyl-lanthionine formation in the lantibiotic precursor.

In another aspect, the present invention provides nucleic acids comprising nucleotide sequences encoding the ORF9 polypeptide (SEQ ID NO: 10), or naturally occurring variants or derivatives of said polypeptide, useful for AviMeCys formation in the antibiotic precursor. In another aspect, the present invention provides nucleic acids comprising nucleotide sequences encoding the ORF15 polypeptide (SEQ ID NO: 16), or naturally occurring variants or derivatives of said polypeptide, useful for the chlorinating the tryptophan residue in the lantibiotic precursor.

In yet another aspect, the present invention provides nucleic acids comprising nucleotide sequences encoding the ORF2 polypeptide (SEQ ID NO: 3), or naturally occurring variants or derivatives of said polypeptide, useful for hydroxylating the proline residue in the lantibiotic precursor.

In another aspect, the present invention provides nucleic acids comprising nucleotide sequences encoding the polypeptides specified by ORFs 1, 10 to 11, 13 to 14 and 17 (SEQ ID NOS: 2, 11 to 12, 14 to 15, and 18), or naturally or artificially occurring variants or derivatives of said polypeptides, useful for export out of the cells of 107891 or a 107891 precursor.

In another aspect, the present invention provides nucleic acids comprising nucleotide sequences encoding the ORFs 3 and 5 polypeptides (SEQ ID NO: 4 and 6), or naturally or artificially occurring variants or derivatives of said polypeptides, useful for regulating lantibiotic production.

In one embodiment, the present invention provides a lantibiotic-producing strain carrying extra copies of the nucleotide sequences specifying at least one ORF selected from any of ORFs 1 through 17 (SEQ ID NOS: 2 to 18).

In one preferred embodiment, such lantibiotic-producing strain is any strain belonging to the order Actinomycetales.

In yet another preferred embodiment, such lantibiotic producing strain is a member of the genus *Microbispora*.

In one preferred embodiment, the present invention provides a *Microbispora* strain containing one or more variations in the nucleotide sequence specified in SEQ ID NO: 1, such variation resulting in an increased or decreased expression of one or more of ORFs 1 through 17 (SEQ ID NOS: 2 to 18).

In one preferred embodiment, the present invention provides nucleic acids comprising a nucleotide sequence specified by SEQ ID NO: 1, or a portion thereof, carried on one or more vectors, useful for the production of 107891, one or more of its precursors or a derivative thereof by another cell.

In one preferred embodiment, said nucleotide sequence or portion thereof is carried on a single vector. Suitable vector are any cosmid, fosmid, BAC, PAC, ESAC vector capable of carrying the entire mlb cluster as defined herein. Suitable vectors are well known to those skilled in the art and described in the literature (Kieser et al., 2000, and references described therein).

In one aspect, the present invention provides a method for increasing the production of 107891, said method comprising the following steps:
 transforming with a recombinant DNA vector a microorganism that produces 107891 or homologues thereof or precursors of 107891 or homologues thereof by means of a biosynthetic pathway, said vector comprising a DNA sequence, chosen from any of ORFs 1 through 17 (SEQ ID NO: 2 through 18), that codes for an activity that is rate limiting in said pathway;
 culturing said microorganism transformed with said vector under conditions suitable for cell growth, expressing said gene and producing said antibiotic or antibiotic precursor.

Suitable host cell are Actinomycetales, to the families Streptosporangiaceae, Micromonosporaceae, Pseudonocardiaceae and Streptomycetaceae, to the genera *Microbispora, Actinoplanes, Planomonospora, Streptomyces* and the like.

In another aspect, the present invention provides a method for producing derivatives of 107891 and homologues thereof, said method comprising the following steps:
 cloning in a suitable vector a segment chosen from the nucleotide sequence defined by SEQ ID NO:1, said segment containing at least a portion of one of ORFs 1 through 17 (SEQ ID NO: 2 through 18), said ORF encoding a polypeptide that catalyzes a biosynthetic step that one wishes to bypass;
 inactivating said ORF by removing or replacing one or more codons that specify for amino acids that are essential for the activity of said polypeptide;

transforming with said recombinant DNA vector a microorganism that produces 107891 or homologues thereof or 107891 precursor thereof by means of a biosynthetic pathway;

screening the resulting transformants for those where said DNA sequence has been replaced by the mutated copy;

culturing mutant cells under conditions suitable for cell growth, expressing of said pathway and producing of said pathway analogue.

In yet another aspect, the present invention provides a method for producing novel lantibiotics, said method comprising the following steps:

transforming with a recombinant DNA vector a microorganism that produces a lantibiotic or homologues thereof or precursor thereof by means of a biosynthetic pathway, said vector comprising one or more ORFs, chosen among ORFs 1 through 17 (SEQ ID NOS: 2 through 18), that codes for enzyme(s) capable of modifying said lantibiotic or lantibiotic precursor;

culturing said microorganism transformed with said vector under conditions suitable for cell growth, expression of said gene and production of said lantibiotic or homologues thereof or lantibiotic precursor thereof.

In yet another aspect, the present invention provides a method for producing novel lantibiotics, said method comprising the following steps:

transforming with a recombinant DNA vector a microorganism, said vector comprising one or more ORFs, chosen among ORFs 1 through 17 (SEQ ID NOS: 2 through 18), that codes for enzyme(s) capable of modifying a lantibiotic or lantibiotic precursor;

culturing said microorganism transformed with said vector under conditions suitable for cell growth, expressing of said gene, in the presence of said lantibiotic or lantibiotic precursor.

In yet another aspect, the present invention provides a method for producing novel lantibiotics, said method comprising the following steps:

transforming with a recombinant DNA vector a microorganism, said vector comprising one or more ORFs, chosen among ORFs 1 through 17 (SEQ ID NOS: 2 through 18), that codes for one or more polypeptides that modify a lantibiotic or lantibiotic precursor;

preparing a cell extract or cell fraction of said microorganism under conditions suitable for the presence of active polypeptide(s), said cell extract or cell fraction containing at least said polypeptide(s);

adding a lantibiotic or lantibiotic precursor to said cell extract or cell fraction, and incubating said mixture under conditions where said polypeptide(s) can modify said lantibiotic or lantibiotic precursor.

A further aspect of this invention includes an isolated polypeptide involved in the biosynthetic pathway of 107891 selected from an ORF polypeptide encoded by any one of mlb ORFs 1 to 17 (SEQ ID NOS: 2 through 18) and a polypeptide which is at least, over its full length, 65%, preferably 95% or more, identical in amino acid sequence to a polypeptide encoded by any one of mlb ORFs 1 to 17 (SEQ ID NOS: 2 through 18), preferably by any one of the mlb ORFs 1 to 3, 5 to 11, 13 to 17 (SEQ ID NOS: 2 to 4, 6 to 12, 14 to 18).

A preferred group of polypeptides comprises any ORF polypeptide encoded by any of the mlb ORFs 1 to 3, 5 to 11, 13 to 17 (SEQ ID NOS: 2 to 4, 6 to 12, 14 to 18), or any polypeptide which is at least, over its full length, 65%, preferably 86%, more preferably 90%, most preferably 95% or more, identical in amino acid sequence to a polypeptide encoded by any of said mlb ORFs.

DEFINITIONS

The term "isolated nucleic acid" herein refers to a DNA molecule, either as genomic DNA or a complementary DNA (cDNA), which can be single or double stranded, of natural or synthetic origin. This term refers also to an RNA molecule, of natural or synthetic origin.

The term "nucleotide sequence" herein refers to full length or partial length sequences of ORFs and intergenic regions as disclosed herein.

The term "nucleotide sequence" herein is also referred to and/or comprises any one of the nucleotide sequence of the invention as show in the sequence listing. Any one of the nucleotide sequences of the sequence listing is A) a coding sequence,
B) an RNA molecule derived from transcription of (A),
C) a coding sequence which uses the degeneracy of the genetic code to encode an identical polypeptide,
D) an intergenic region, containing promoters, enhancers, terminator and antiterminator sequences.

The terms "gene cluster", "cluster" and "biosynthesis cluster" herein designate a contiguous segment of a microorganism's genome that contains all the genes required for the synthesis of a secondary metabolite.

The term "mlb" herein refers to a genetic element responsible for 107891 biosynthesis in *Microbispora* sp. PTA-5024. The term is an acronym of Microbispora LantiBiotic.

The term "ORF" herein refers to a genomic nucleotide sequence that encodes one polypeptide. In the context of the present invention, the term ORF is synonymous with "gene".

The term "ORF polypeptide" herein refers to a polypeptide encoded by an ORF.

The term "mlb ORF" herein refers to an ORF comprised within the nab gene cluster.

The term "secondary metabolite" herein refers to a bioactive substance produced by a microorganism through the expression of a set of genes specified by a gene cluster.

The term "vector" herein is defined to include, inter alia, any plasmid, cosmid, phage, which can transform prokaryotic host by integration into the cellular genome or exist extrachromosomally (e.g. autonomous replicating plasmid with an origin of replication)

The term "production host", "host cell" herein is a microorganism where the formation of a secondary metabolite is directed by a gene cluster derived from a donor organism.

The term "homologue" herein refers to a polypeptide, encoded by a biosynthetic gene cluster, which shares at least 65% sequence identity over its entire length with any of the polypeptides encoded by the mlb cluster.

BRIEF DESCRIPTION OF THE DRAWINGS

FIG. 4 shows the main features of the ORFs.

Figure 1:
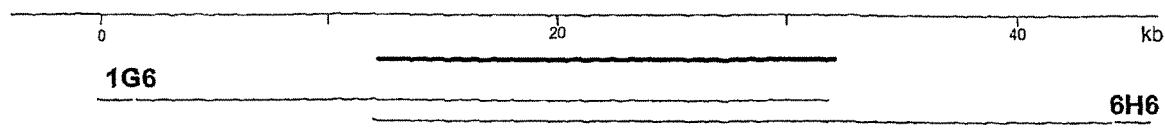
FIG. 1 shows isolated DNA segments derived from the chromosome of *Microbispora* sp. PTA-5024. The thick line denotes the segment described in SEQ ID NO: 1. The cosmids carrying said isolated DNA segments are designated 1G6 and 6H6.
Figure 2:
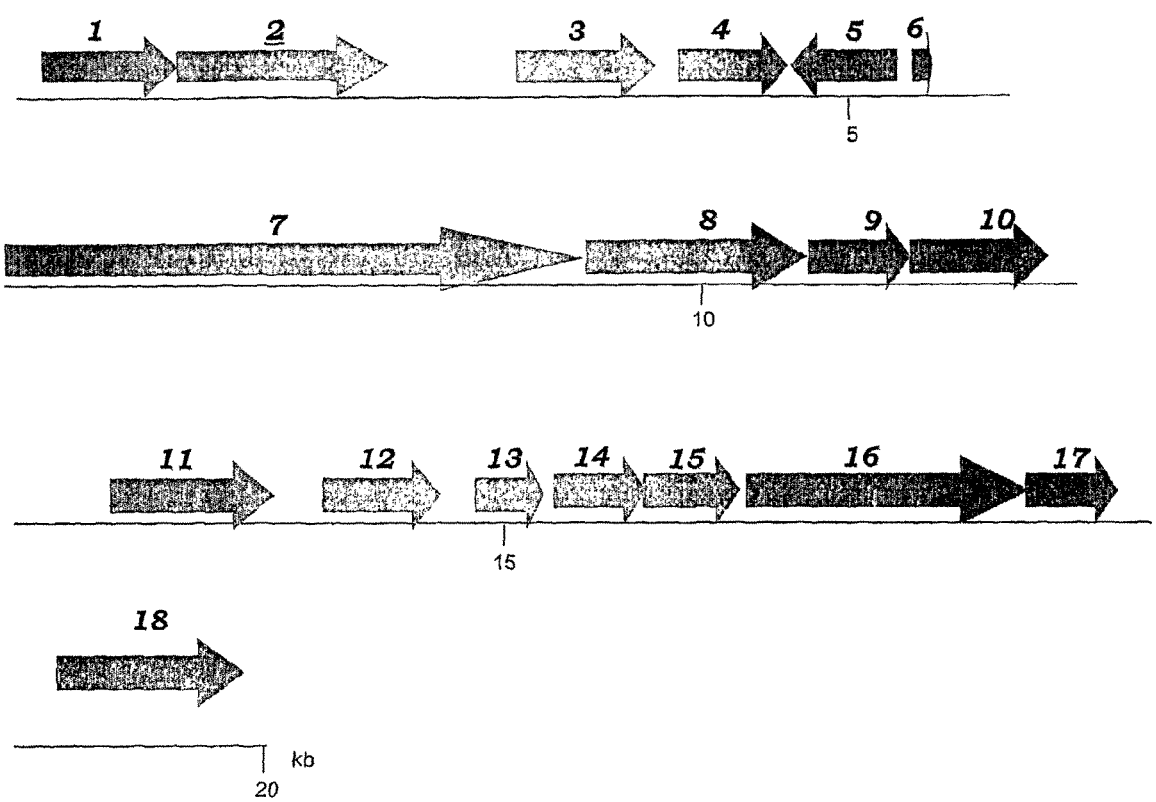
FIG. 2 shows genetic organization of the mlb cluster. Each ORF is represented by an arrow, and numbered as in Table 1 (FIG. 4). The orientation is the same as in FIG. 1. Numbers on the scale bars indicate sequence coordinates (in kb).
Figure 3:
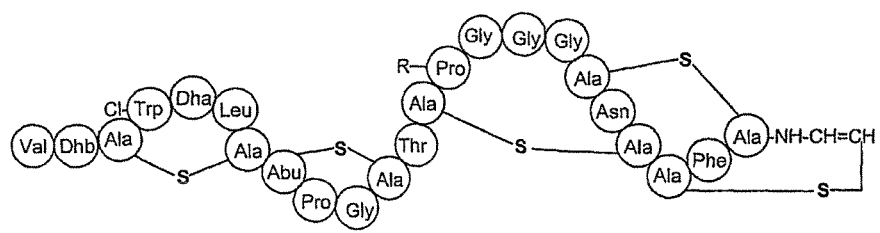
FIG. 3 shows structure of the components of the 107891 complex.

A. The Mlb Genes Isolated from Microbispora 107891 is a complex of closely related peptide antibiotics produced by *Microbispora* sp. PTA-5024. The present invention provides nucleic acid sequences and characterization of the mlb gene cluster for 107891 biosynthesis. The physical organization of the mlb gene cluster, together with flanking DNA sequences, is reported in FIG. 1, which illustrates the physical map of a 20-kb genomic segment from the genome of *Microbispora* sp. PTA-5024, together with two cosmids defining such segment. The genetic organization of the DNA segment governing 107891 biosynthesis is shown in FIG. 2 and its nucleotide sequence is reported as SEQ ID NO: 1.

The precise boundary of the cluster can be established from the functions of its gene products. Therefore, on the left end (FIG. 1), the mlb cluster is delimited by mlb ORF1, encoding the ABC transporter (SEQ ID No: 2), involved in the export of 107891. On the right side, the mlb cluster is delimited by mlb ORF17, a membrane ion antiporter (SEQ ID No: 18). The mlb cluster spans approximately 20,000 base pairs and contains 17 ORFs, designated mlb ORF1 through mlb ORF17. The contiguous nucleotide sequence of SEQ ID NO: 1 (20000 base pairs) encodes the 17 deduced proteins listed in SEQ ID NOS: 2 to 18.

- ORF1 (SEQ ID NO: 2) represents 300 amino acids deduced from translating SEQ ID NO: 1 from nucleotides 67 to 969.
- ORF2 (SEQ ID NO: 3) represents 414 amino acids deduced from translating SEQ ID NO: 1 from nucleotides 966 to 2210.
- ORF3 (SEQ ID NO: 4) represents 260 amino acids deduced from translating SEQ ID NO: 1 from nucleotides 2941 to 3723.
- ORF4 (SEQ ID NO: 5) represents 221 amino acids deduced from translating SEQ ID NO: 1 from nucleotides 3948 to 4614.
- ORF5 (SEQ ID NO: 6) represents 220 amino acids deduced from translating SEQ ID NO: 1 from nucleotides 5283 to 4621 on the complementary strand.
- ORF6 (SEQ ID NO: 7) represents 57 amino acids deduced from translating SEQ ID NO: 1 from nucleotides 5414 to 5587.
- ORF7 (SEQ ID NO: 8) represents 1115 amino acids deduced from translating SEQ ID NO: 1 from nucleotides 5706 to 9053.
- ORF8 (SEQ ID NO: 9) represents 475 amino acids deduced from translating SEQ ID NO: 1 from nucleotides 9080 to 10507.
- ORF9 (SEQ ID NO: 10) represents 215 amino acids deduced from translating SEQ ID NO: 1 from nucleotides 10537 to 11184.
- ORF10 (SEQ JD NO: 11) represents 316 amino acids deduced from translating SEQ ID NO: 1 from nucleotides 11181 to 12131.
- ORF11 (SEQ ID NO: 12) represents 242 amino acids deduced from translating SEQ ID NO: 1 from nucleotides 12253 to 12981,
- ORF12 (SEQ ID NO: 13) represents 211 amino acids deduced from translating SEQ ID NO: 1 from nucleotides 13357 to 13992.
- ORF13 (SEQ ID NO: 14) represents 249 amino acids deduced from translating SEQ ID NO: 1 from nucleotides 14795 to 15544.
- ORF14 (SEQ ID NO: 15) represents 236 amino acids deduced from translating SEQ ID NO: 1 from nucleotides 15546 to 16256.
- ORF15 (SEQ ID NO: 16) represents 541 amino acids deduced from translating SEQ ID NO: 1 from nucleotides 16370 to 17995.
- ORF16 (SEQ ID NO: 17) represents 178 amino acids deduced from translating SEQ ID NO: 1 from nucleotides 17992 to 18528.
- ORF17 (SEQ ID NO: 18) represents 430 amino acids deduced from translating SEQ ID NO: 1 from nucleotides 18525 to 19817.

The Genomic Organization and Primary Sequence of the Mlb Cluster Places 107891 in Type-A Lantibiotics.

Comparison between mlb and other lantibiotic gene clusters reveals important differences. In fact, the mlb cluster is characterized by the presence of several ORFs that do not find homologs in other lantibiotic clusters. These include mlb ORFs 1 through 6, 12, 15 through 18 (SEQ ID NOS: 2 through 7, 13, 16 through 19). In conclusion, the organization of the mlb cluster as described herein is substantially different from those of other clusters involved in the synthesis of other lantibiotic. It therefore represents the first example of a cluster with such a genomic organization.

B. Roles of the mlb genes

The present invention discloses the DNA sequence responsible for the synthesis of the prepropeptide precursor of 107891. The 107891 prepropeptide consists of a leader peptide, 33-aa long, and of a 24-aa propeptide. The nucleic acid sequences referred to herein are those encoding the 107891 prepropeptide or fragments thereof. The 57-aa 107891 prepropeptide represents a novel element that shows only, over its entire length, 41% identity with UniProt accession number P21838, the prepropeptide of the lantibiotic gallidermin from *Staphylococcus gallinarum*.

Other genes present in the mlb cluster represent novel genetic elements useful for increasing production of 107891 or for synthesizing novel metabolites. Among these, mlb ORFs 7 to 8 (SEQ ID NO: 8 through 9) encode the proteins involved in post-translational modification of the translation product of mlb ORF6, to introduce the lanthionine residues in mature 107891. In particular, the mlb ORF7 polypeptide is responsible for dehydration of the Ser and Thr residues in the prepropeptide portion of 107891 to generate dehydroalanine and dehybutyrine residues, respectively. The mlb ORF8 polypeptide catalyzes the nucleophilic attack of cysteine residues within the prepropeptide onto the dehydro amino acid residues. These genes can be cloned and expressed in a heterologous host to yield active enzymes capable of introducing lanthionine residue to other prepropeptides.

Yet other preferred nucleic acid molecules of the present invention include mlb ORF9 (SEQ ID NO: 10) that encodes a protein involved in the oxidative decarboxylation yielding the S—[(Z)-2-aminovinyl]-(3S)-3-methyl-D-cysteine residue (Formula I).

Yet other preferred nucleic acid molecules of the present invention include mlb ORF16 (SEQ ID NO: 17) that encodes a tryptophan halogenase, responsible for the addition of a chlorine atom to amino acid 4 of 107891. mlb ORF16 represents a novel and unique genetic element, previously not reported in other lantibiotic clusters. Indeed, chlorination is a rather unique feature of 107891 among known lantibiotics. This gene can be cloned and expressed in a heterologous host to yield an active enzyme capable of chlorinating tryptophan residues of lantibiotic molecules. Alternatively, mlb ORF16 can be inactivated in the producing strain, resulting in the formation of 107891 derivatives devoid of the chlorine attached to amino acid 4.

Yet other preferred nucleic acid molecules of the present invention include mlb ORF2 (SEQ ID NO: 3 that encodes a cytochrome P450 hydroxylase responsible for post-translational modification of the 107891 prepropeptide, by the addition of one or two oxygen(s) to the proline residue at position 14. mlb ORF2 represents a novel and unique genetic element, that has never been reported in other lantibiotic clusters. Indeed, the 107891 proline hydroxylation profile is rather unique among lantibiotics. This gene can be cloned and expressed in a heterologous host to yield an active enzyme capable of oxidizing proline residues present in a lantibiotic molecule. Alternatively, mlb ORF2 can be inactivated in the producing strain, resulting in the formation of 107891 derivatives devoid of oxygen atoms at amino acid 14.

The mlb cluster also includes a number of regulatory genes, responsible for activating, directly or indirectly, the expression of biosynthesis and resistance genes during 107891 production. These genes include mlb ORFs 3 and 5 (SEQ ID NOS: 4 and 6): mlb ORF3 (SEQ ID NO: 4) represents a separate quorum-sensing peptide, responsible, in part, for the regulation of 107891 production; and mlb ORF5 (SEQ ID NO: 6) is highly related to Sigma-70, an extracytoplasmic function family of RNA polymerase sigma factors that act as positive transcriptional regulator. mlb ORFs 3 and 5 represent novel genetic elements, absent from other lantibiotic clusters. The two genes, mlb ORF 3 and 5, can be cloned and expressed, either individually or in any combination of them, in another lantibiotic producer strains to increase the yield of product formed.

Host strains include but are not limited to strains belonging to the order Actinomycetales, to the families Streptosporangiaceae, Micromonosporaceae, Pseudonocardiaceae and Streptomycetaceae, to the genera *Microbispora, Actinoplanes, Planomonospora, Streptomyces* and the like. Alternatively, these genes can be overexpressed, individually or in any combination of them, in the 107891 producing strain to increase the yield of 107891.

The mlb cluster also includes a number of genes responsible for exporting lantibiotic intermediates or finished products out of the cytoplasm and for conferring resistance to the producer cell. These genes include mlb ORFs 1, 10 to 11, 13 to 14 and 17 (SEQ ID NOS: 2, 11 to 12, 14 to 15 and 18). mlb ORFs 1, 10 to 11, 13 to 14 encode transporters of the ABC class, responsible for the ATP-dependent excretion of 107891 or its intermediates. mlb ORF17 encodes an Na/K ion-antiporter, responsible for exporting 107891 or its intermediates against a proton gradient. These genes can be cloned and expressed, either individually or in any combination of them, in another lantibiotic producer strain to increase the yield of product formed. Host strains include but are not limited to strains belonging to the order Actinomycetales, to the families Streptosporangiaceae, Micromonosporaceae, Pseudonocardiaceae and Streptomycetaceae, to the genera *Microbispora, Actinoplanes, Planomonospora, Streptomyces* and the like.

Alternatively, these genes can be overexpressed, individually or in any combination of them, in the 107891 producing strain to increase the yield of 107891.

C. Uses of the Mlb Cluster

The present invention provides also nucleic acids for the expression of the entire 107891 molecule, any of its precursors or a derivative thereof. Such nucleic acids include isolated gene cluster(s) comprising ORFs encoding polypeptides sufficient to direct the assembly of 107891. In one example, the entire mlb cluster (SEQ ID NO: 1) can be introduced into a suitable vector and used to transform a desired production host. In another aspect, the mlb cluster is cloned as two separate segments into two distinct vectors, which can be compatible in the desired production host. In yet another aspect, the mlb cluster can be subdivided into three segments, each cloned into a separate, compatible vector. Examples of the use of one-, two- or three-vector systems have been described in the literature.

Once the mlb cluster has been suitably cloned into one or more vectors, it can be introduced into a number of suitable production hosts, where production of lantibiotics might occur with greater efficiency than in the native host. Preferred host cells are those of species or strains that can efficiently express actinomycetes genes. Such host include but are not limited to Actinomycetales, Streptosporangiaceae, Micromonosporaceae, Pseudonocardiaceae and Streptomycetaceae, *Microbispora, Actinoplanes, Planomonospora and Streptomyces* and the like. Alternatively, a second copy of the mil) cluster, cloned into one or more suitable vectors, can be introduced the 107891 producing strain, where the second copy of mlb genes will increase the yield of 107891.

The transfer of the producing capability to a well characterized host can substantially improve several portions of the process of lead optimization and development: the titer of the natural product in the producing strain can be more effectively increased; the purification of the natural product can be carried out in a known background of possible interfering activities; the composition of the complex can be more effectively controlled; altered derivatives of the natural product can be more effectively produced through manipulation of the fermentation conditions or by pathway engineering.

Alternatively, the biosynthetic gene cluster can be modified, inserted into a host cell and used to synthesize or chemically modify a wide variety of metabolites: for example the open reading frames can be re-ordered, modified and combined with other lantibiotic biosynthesis gene cluster.

Using the information provided herein, cloning and expression of 107891 nucleic acids can be accomplished using routine and well known methods.

In another possible use, selected ORFs from the mlb gene cluster are isolated and inactivated by the use of routine molecular biology techniques. The mutated ORF, cloned in a suitable vector containing DNA segments that flank said ORF in the *Microbispora* sp, PTA-5024 chromosome, is introduced into said Microbispora strain, where two double crossover events of homologous recombination result in the inactivation of said ORF in the producer strain. This procedure is useful for the production of precursors or derivatives of 107891 in an efficient manner.

In another possible use, selected ORFs from the mlb gene cluster are isolated and placed under the control of a desirable promoter. The engineered ORF, cloned in a suitable vector, is then introduced into *Microbispora* sp. PTA-5024, either by replacing the original ORF as described above, or as an additional copy of said ORF. This procedure is useful for increasing or decreasing the expression level of ORFs that are critical for production of the 107891 molecule, precursors or derivatives thereof.

Experimental Section

The following examples serve to illustrate the principles and methodologies through which the 107891 gene cluster is identified and the principles and methodologies through which all the mlb genes are identified and analyzed. These examples serve to illustrate the principles and methodologies of the present invention, but are not meant to limit its scope.

General Methods

Unless otherwise indicated, bacterial strains and cloning vectors can all be obtained from public collections or commercial sources. Standard procedures are used for molecular biology. Microbispora was grown in HT agar and in V6 medium (20 g/l glucose, 5 g/l yeast extract, 3 g/l casein hydrolysate, 5 g/l meat extract, 5 g/l peptone, 1.5 g/l NaCl, 0.5% glycerol). Lantibiotics are isolated following published procedures. Sequence analyses are performed using standard programs. Database searches are performed with Blast or Fasta programs at public sites.

EXAMPLE 1

Isolation of 107891 Biosynthesis Genes

A genomic library is made with DNA from *Microbispora* sp. PTA-5024 in the conjugative cosmid vector Supercos 3. This was constructed by insertion of the aaclV-oriT-intΦC31 cassette from pSET152 into Supercos 1 (Stratagene, La Jolla, Calif. 92037) as follows: the aacW-oriT-intΦC31 cassette is obtained by PCR as a NruI fragment, 3.8 kb long, from the vector pSET152 and inserted into the same site of supercos1. Total DNA from *Microbispora* sp. PTA-5024 is partially digested with Sau3AI in order to optimize fragment sizes in the 40 kb range. The partially digested DNA is treated with alkaline phosphatase and ligated to Supercos3 previously digested with BamHI. The ligation mixture is packaged in vitro and used to transfect *E. coli* XL1Blue cells. The resulting cosmid library is screened by hybridization with the oligonucleotide probe 5'-GTS ACS WSS TGG WSS YTS WSS ACS GGS CCS TGC ACS WSS CCS GGS GGS WSS AAC WSS WSS TCC WSS TG-3' (SEQ ID NO: 19). The oligonucleotide is designed from the amino acid sequence deduced from the structure of 107891. Two cosmids positive to this probe are isolated and physically mapped with restriction enzymes. From such experiments, the cosmids reported in FIG. 1 are identified. The segment thus identified from the genome of *Microbispora* sp. PTA-5024 contains the mlb gene cluster responsible for the synthesis of the antibiotic 107891.

The above example serves to illustrate the principle and methodologies through which the mlb cluster can be isolated. It will occur to those skilled in the art that the mlb cluster can be cloned in a variety of vectors. However, those skilled in the art understand that, given the 20-kb size of the mlb cluster, preferred vectors are those capable of carrying large inserts, such as lambda, cosmid and BAC vectors. Those skilled in the art understand that other probes can be used to identify the mlb cluster from such a library. From the sequence reported in SEQ ID NO: 1, any fragment can be PCR-amplified from *Microbispora* sp. PTA-5024 DNA and used to screen a library made with such DNA. One or more clones from said library can be identified that include any segment covered by SEQ M NO: 1. Furthermore, it is also possible to identify the mlb cluster through the use of heterologous probes, such as those derived from other lan cluster, using the information provided in Table 1. Alternatively, other gene clusters directing the synthesis of secondary metabolites contain genes sufficiently related to the mlb genes as to allow heterologous hybridizations. All these variations fall within the scope of the present invention.

EXAMPLE 2

Sequence Analysis of 107891 Gene Cluster

The mlb cluster, identified as described under Example 1, is sequenced by the shotgun approach. The sequence of the mlb cluster is provided herein as SEQ ID NO: 1. The resulting DNA sequence is analyzed to identify likely coding sequences, which are compared against other lan clusters or searched against GenBank. The exact start codon for each ORF is established by multiple alignment of related sequences or by searching for an upstream ribosomal binding site. In total, 17 ORFs, denominated mlb ORF1 through ORF17, are identified. The results of these analyses are summarized in Table 1, and provided herein in the sequence listing as SEQ ID No: 2 through SEQ ID No: 18. Details are given below.

2A. Synthesis of the 107891 Prepropeptide mlb ORFs 6 is responsible for the synthesis of prepropeptide. The prepropeptide contains a 49-aa leader sequence and a 24-aa propeptide (SEQ ID NOS: 7) which is post-translationally modified to produce the mature lantibiotic. Two common features of lantibiotic leader peptides are preserved in 107891: the conserved sequence of Type-A (antibiotics (e.g. the F-D/N-L-D/E motif) and the proline residue at position-2. The C-terminal part of the prepropeptide (SEQ ID NOS: 7) is in agreement with the published 107891 primary structure and its proposed propeptide sequence.

2B. Post-Translationally Modification of the 107891 Propeptide

Four proteins, encoded by mlb ORFs 7 through 9 (SEQ ID NOS: 8 through 10) and mlb ORF 17 (SEQ ID NOS: 18) are involved in the post-translational modification of the 107891 prepropeptide. Homologs of these gene products are found in many lantibiotic clusters. On the basis of the sequence identities with the dehydratases and cyclases found in other lantibiotic clusters, and their roles, the following predictions can be made. The mlb ORF7 polypeptide is responsible for dehydration of the serine residues at positions 3, 5, 13, 18 and 21 and of the threonine residue at position 2 and 8 of the 107891 propeptide, to generate the corresponding dehydrated residues. The mlb ORF8 polypeptide catalyzes the regio- and stereospecific conjugate addition of the cysteine residues present in the 107891 propeptide to four dehydroalanine and one dehydrobutyrine residues to generate the corresponding five thioethers. Specifically, the mlb ORF8 polypeptide is involved in the formation of the 3-7, 13-20, 18-23 and 21-24 lanthionines and of the 8-11 methylanthionine.

On the basis of the sequence identities observed with the decarboxylases encoded by the epidermin and mersacidin clusters, mlb ORF9 encodes the enzyme responsible for the decarboxylation of the 21-24 lanthionine moiety. On the basis of the sequence identities observed with the flavin reductase encoded by other antibiotic clusters, mlb ORF16 encoded a flavoprotein reductase. Considering the roles predicted for oxidative decarboxylation during epidermin and mersacidin formation, the mlb ORFs 9 and 16 polypeptides catalyze the formation of the 5-[(Z)-2-aminovinyl]-D-cysteine residue present in 107891 (Formula I).

2C. Formation of β-Hydroxyproline and Tryptophan Chlorination

Two proteins, encoded by mlb ORFs 2 and 15 (SEQ ID NOS: 3 and 16) are involved in the addition of one or two β-hydroxyl groups to the proline residue at position 14 and in the chlorination of the tryptophan residue at position 4 of the 107891 propeptide. The mlb ORF2 polypeptide show significant identity to P450 monooxygenases (Table 1) and is involved in hydroxylation of the proline residue. No homologs of mlb ORF2 have been found in other lantibiotic clusters, thereby this gene represents a unique example of a P450 monoxygenase involved in hydroxylation of a lantibiotic molecule. In addition, on the basis of the level of identities with other halogenases, the mlb ORF15 polypeptide is involved tryptophan chlorination and represents a unique example of a halogenase involved in modification of a lantibiotic molecule.

2D. Export and Resistance

Five proteins, encoded by ORFs 1, 10, 11, 13, 14 and 17 (SEQ ID NOS: 2, 11, 12, 14, 15 and 18) are involved in exporting 107891 or its precursor outside the cytoplasm and in conferring resistance to the producing strain. Their predicted roles are as follows.

Homologs of ORF1 (SEQ ID NO: 2) are not found in other lantibiotic clusters. This gene encodes additional ABC-type transporters (Table 1), and is therefore involved in conferring resistance to 107891 in the producing strain *Microbispora* sp. PTA. Homologs of ORFs 10, 13 to 14 and 17 (SEQ ID NOS: 11, 14 to 15 and 18) are present in other lantibiotic clusters (Table 1). They encode ABC-type and ion-dependent transmembrane transporters, respectively. They are thus involved in export and/or compartimentalization of 107891 or its precursors. mlb ORF17 encodes an Na/K ion-antiporter, responsible for exporting 107891 or its intermediates against a proton gradient.

2E. Regulation

Two proteins, encoded by ORFs 3 and 5 (SEQ ID NOS: 4 and 6), are involved in regulating the expression of one or more of the mlb genes. The mlb ORF5 polypeptide (SEQ ID NO: 6) represents a novel genetic element, homologs of which are not found in the other lantibiotic clusters. This protein belongs to the extracytoplasmic function family of sigma factors that act as positive transcriptional regulators. The ORF3 polypeptide (SEQ ID NO: 4) belongs to the family of LuxR-type transcriptional regulators. ORFs 3 (SEQ ID NOS: 4) is therefore likely to be required for the expression of one or more of the mlb genes.

2F. Additional Functions

Two additional ORFs are present in the mlb cluster: ORF4 (SEQ ID NO: 5) and ORF12 (SEQ ID NO: 13). Both ORFs are related to proteins of unknown function present in *Salinispora tropica* and *Streptomyces ambofaciens*, respectively (Table 1). However, their precise role in 107891 biosynthesis cannot be predicted yet.

EXAMPLE 3

Manipulation of the 107891 Pathway by Gene Replacement

Using the information provided in Example 2, an in frame deletion in ORF 2 is constructed as follows. Fragment A was obtained through amplification with oligos 5'-AAGCTTG-CATCTGCGTGGGCGTCCTGC-3' (SEQ ID NO: 20) and 5'-TCTAGACGGTCCGAAGATCATGGCCGCGG-3' (SEQ ID NO: 21); and fragment B is obtained through amplification with oligos 5'-TCTAGATCCATGTGAACCGGCGGGTG-GCCG-3' (SEQ ID NO: 22) and 5'-GAATTCCG-GTCGCTCTCCTCGTCCTTTGCC-3' (SEQ ID NO: 23)

Next, fragment A is digested with EcoRI and XbaI, fragment B with XbaI and HindIII, and both are ligated to pSET152 previously digested with EcoRI and HindIII. After transformation of *E. coli* DH5α cells, the resulting plasmid, designated pDM1, is recognized by the presence of fragments of 4 kb and 1.5 kb after digestion with EcoRI and HindIII. An aliquot of pDM1 is transferred into *E. coli* ET12567 (PUB307) cells, yielding strain DM1. Then, about $10^8$ CFU of DM1 cells, from an overnight culture in LB, are mixed with about $10^7$ CFU of Microbispora PTA 5024 grown in Rare3 medium for about 80 h. The resulting mixture is spread onto HT plates, which are then incubated at 28° C. for about 20 h. After removing excess *E. coli* cells with a gentle wash with water, plates are overlaid with 3 ml soft agar containing 200 µg nalidixic acid and 15 µg/ml apramycin. After further incubation at 28° C. for 3-5 weeks, Microbispora ex-conjugants are streaked onto fresh medium containing apramycin. One such ex-conjugant, named strain Mb-DM1, is further processed. Strain Mb-DM1 is then grown for several passages in HT medium without apramycin and appropriate dilutions are plated on HT agar without apramycin. Individual colonies are then analyzed by PCR, using oligos 5'-CGCGCT-GCTCGGGGCCAAC-3' (SEQ ID NO: 24) and 5'-AG-GAAACGGCCAGCCCGTGG-3' (SEQ ID NO: 25).

Colonies containing the deleted allele of ORF2 are recognized by the presence of a 1.5 kb band. One such colony, designated Mb-DM2, is grown in HT medium and the formation of dehydroxyl-107891 is confirmed by comparison with an authentic standard.

The above example serves to illustrate the principle and methodologies through which an ORF chosen among any of those specified by SEQ ID NOS: 2 to 18 can be replaced by a mutated copy in the 107891 producing strain *Microbispora* sp. PTA 5024. It will occur to those skilled in the art that ORF2 (SEQ ID NO: 3) is just an example of the methodologies for creating in frame deletions in the cluster specified by SEQ ID NO: 1.

Those skilled in the art understand also that in frame-deletions are just one method for generating mutations, and that other methods including but not limited to frame-shift mutations, insertions and site-directed mutations can also be used to generate null mutants in any of the ORFs specified by SEQ ID NOS: 2 to 18

Those skilled in the art also understand that, having established a method for generating mutations in any of the ORFs specified by SEQ ID NOS: 1, these same methodologies can be applied for altering the expression levels of these same ORFs. Examples for how this can be achieved include but are not limited to integration of multiple copies of said ORFs into any place in the *Microbispora* sp. PTA 5024 genome, alteration in the promoters controlling the expression of said ORFs, removal of antisense RNAs or transcription terminators interfering with their expression.

Finally, variations in the vectors used for introducing the mutated alleles into *Microbispora* sp. PTA5024, in the conditions for conjugation and cultivation of the donor and recipient strain, in the method for selecting and screening ex-conjugants and their derivatives, all fall within the scope of the present invention.

EXAMPLE 4

In Vitro Halogenation of a Lantibiotic

Using the information provided in Example 2, mlb ORF15 (SEQ ID NO: 16) is overexpressed in *E. coli* as follows. A 1.6 kb fragment, obtained by amplification with oligos 5'-TTTTTCATATGGGTGGGAGTGATCGGCGGCG-3' (SEQ ID NO: 26) and 5'-TTTTTGTCGACCTACTGCTG-GCCGCGGTCCGGACT-3' (SEQ ID NO: 27), is digested with NcoI and SalI and ligated to pET22b, previously digested with NcoI and XhoI. After transformation of *E. coli* DH5a cells, the resulting plasmid pHAL, recognizable for the presence of fragments of 5.5 kb and 1.6 kb after digestion with NdeI and XhoI, is introduced into *E. coli* BL21(DE3) cells. Cultures of *E. coli* BL21(DE3) cells harbouring pHAL are grown at 20° C. in LB to an OD600 of 0.6. Then, IPTG is added to 1 mM and cells grown for further 6 h. Cells are harvested, ruptured by sonication and the His-tagged ORF15 polypeptide recovered from a Ni-agarose column. In vitro halogenation of substrates, such as lacticin 481 or 97518 is carried out and formation of the chlorine-derivative of the lantibiotic is established by MS analysis.

The above example serves to illustrate the principle and methodologies through which an ORF chosen among any of those specified by SEQ ID NOS: 2 to 18 can be overexpressed in a convenient host, the resulting enzyme overproduced and used for transforming a lantibiotic natural product into a different compound. It will occur to those skilled in the art that ORF15 (SEQ ID NO: 16) is just used as an example of the methodologies for overproducing any polypeptide encoded by SEQ ID NO: 1. Those skilled in the art understand also that other methods for overproducing proteins, including but not limited to the use of different affinity tags, the use of different vectors, of different host strains, and of methods of induction, can also be used to overproduce the polypeptides specified by ORFs 1 to 17 (SEQ ID NOS: 2 to 18).

It will occur to those skilled in the art that other lantibiotic substrates containing or not triptophan residue, can be used for adding chlorine atoms by ORF15 (SEQ ID NO: 16). It will also occur to those skilled in the art that other ORF polipeptides specified by mlb cluster (SEQ ID NO: 1) can be used for the post-translational modification of other lantibiotic pre-propeptides. ORF polipeptides that can be used for this purpose include but are not limited to ORF2 (SEQ ID NO 3). Specifically, ORFs 7 and 8 (SEQ ID NO 8 and 9) can be used to dehydrate and introduce thioether bridges in other lantibiotic prepropeptides; ORFs 9 and 16 (SEQ ID NO 10 and 17) can be used to decarboxylate other lantibiotic containing a C-terminal Cys residue; and ORF 2 (SEQ ID NO 3) can be used to hydroxylate other proline containing lantibiotics.

EXAMPLE 5

Expression of the mlb Cluster in a Heterologous Host

Using the information provided in Examples 1 and 2, cosmid 1G6 (FIG. 1) containing the entire mlb cluster (SEQ JD NO: 1) is introduced into *Streptomyces albus* by conjugation as described by Kieser et al., 2000. Apramycin resistant exconjugants are grown under appropriate conditions and 107891 is purified as described.

Those skilled in the art understand also that *S. albus* is just one producer strain, and that other strains can also be used for introducing the entire mlb cluster (SEQ ID NO: 1) and for the production of 107891. Preferred host cells are those of species or strains that can efficiently express actinomycete genes. Such host include but are not limited to Actinomycetales, Streptosporangiaceae, Micromonosporaceae, Pseudonocardiaceae and Streptomycetaceae, *Microbispora, Actinoplanes, Planomonospora* and *Streptomyces* and the like. Those skilled in the art understand that, provided that suitable promoters are placed in front of mlb operons, production hosts need not to be limited to those cells that can efficiently expressed actinomycete genes. Suitable production hosts of this latter category can be found among those that are easy to manipulate genetically or among those that naturally produce other lantibiotics. Examples of such production hosts include but not limited to *Escherichia coli* and related species, *Bacillus* spp., *Streptococcus spp, Lactobacillus* spp., *Staphylococcus* spp., and the like.

Those skilled in the art understand also that using the methodologies described in this example, the mlb cluster can be introduced as a second copy into the original 107891 producer strain *Microbispora* sp. PTA 5024 where the second copy of the mlb genes will increase the yield of 107891.

Those skilled in the art understand also that different vectors, different methodologies for introducing the mlb cluster, different methods of selecting recombinant clones carrying the mlb cluster, different methods and conditions for growing said recombinant clones and different methods for detecting 107891 production, can be effective for expression of the mlb cluster in a heterologous host.

EXAMPLE 6

Generation of a Library of 107891 Variants

Using the information provided in Examples 2, 3 and 5, mlb ORF 6 (SEQ ID NO: 7) is modified to produce variants of 107891 as follows. First, a vector carrying an in frame deletion in ORF 6 (SEQ ID NO: 7) is constructed according to the methodologies of Example 3 utilizing OLIGOS 5'-GCAGC-CAGGCTCGCACCGGC-3' and CGCCCGTAACGAGCGA (SEQ ID NO 28 and 29) for fragment A and OLIGOS 5'-GCAGCTTCTGCTGCTGA-3' and 5'-TCCCGGCCAGC-CACTT-3' (SEQ ID NO 30 and 31) for fragment B to amplify ORF 6. The resulting construct is used to replace ORF 6 in the *S. albus* strain obtained as described on Example 5 according to the methodologies of Example 3 and generating SA-D6 strain. Next, the prepeptide portion of mlb ORF6 (SEQ ID NO: 7), obtained by amplification with oligos 5'-CCG-GAAAGGAGCGAGCATATG-3' (SEQ ID NO: 32) and 5'-CAGATCTGCCAATACAGT-3' (SEQ ID NO: 33), is digested with NdeI and BglII and ligated to pIJ8600 (Kieser et al., 2000), previously digested with NdeI and BglII generating plasmid pPRE1. In a parallel experiment oligos A 5'-C GGT GTC GAG GAG ATC ACC GCC GGG CCG GCG NNN NNN AGC NNN NNN NNN TGC ACC NNN NNN TGC NNN AGC NNN NNN NNN NNN AGC NNN TGC AGC NNN TGC TOG TGA AGA TCT-3' and oligo B 5'-T TCA GCA GCA NNN GCT GCA NNN GCT NNN NNN NNN NNN GCT NNN GCA NNN NNN GGT GCA NNN NNN NNN GCT NNN NNN CGC CGG CCC GGC GGT GAT CTC CTC GAC ACC GAT CGA-3' (SEQ ID 34 and 35) are denatured and annealed to generate a mixture of DNA segments (SEQ ID NO: 36) which encodes polypeptides with all possible changes in the amino acid sequence of the propetide region of the ORF6 polipeptide expect for those involved in thioether formation (specifically amino acid 3, 7, 8, 11, 13, 18, 20, 21, 23 and 24). This mixture of DNA segments is ligated to plasmid pPRE1, previously digested with BSA OI and BglII, to generate a library of plasmids carrying all possible variant forms (expect for the (methyl)lanthionine bridges) of the ORF 6 segment encoding the propeptide fused to the ORF 6 segment encoding the leader peptide. This plasmid library is introduced into SA-D6 strain and the resulting exconjugants, grown in the presence of μg/ml thiostrepton, are screened for the production of 107891 variants by biological assays or HPLC analysis. Interesting variants are further characterized by sequencing the propeptide portion of the ORF 6 variant and by structure elucidation.

Those skilled in the art understand that the leader peptides portion of the ORF 6 polipeptide can also be modified insofar as the enzymes involved in post-translational modifications (SEQ ID NO: 8 and 9) can recognize said different leader peptides. Variations in the leader peptide portion of the ORF 6 polipeptide fall within the scope of this invention.

It will occur to those skilled in the art that other method can be used for constructing a library of ORF 6 variants, including but not limited to the use of different oligos, vectors, induction system and host strains. Furthermore those skill in the art understand that methyllanthionine residues can be replaced by lanthionine residues, and viceversa, to generate additional ORF 6 variants. Those skill in the art understand also that site directed mutagenesis can be used to generate selected variants of ORF 6 resulting in the production of specified derivatives of 107891.

The invention claim is:

1. A recombinant DNA vector which comprises the nucleotide sequence SEQ ID NO:1.

2. A host cell transformed with the vector of claim 1.

3. The transformed host cell of claim 2 which belongs to the order Actinomycetales.

4. The transformed host cell of claim 3 which belongs to the family selected from the group consisting of Streptosporangiaceae, Micromonosporaceae, Pseudonocardiaceae and Streptomycetaceae.

5. The transformed host cell according to claim 4 which belongs to the genera selected from the group consisting of *Microbispora, Actnopanes, Planomonospora*, and *Streptomyces*.

6. The transformed host cell of claim 2 which belongs to the order Bacillales.

7. The transformed host cell of cam 6 which belongs to the family selected from the group consisting of Bacillaceae, Lactobacillaceae, Streptococcaceae and Staphylococcaceae.

8. The transformed host cell of claim 7 which belongs to the genera selected from the group consisting of *Bacillus, Lactococcus, Streptococcus*, and *Staphylococcus*.

9. The transformed host cell of claim 2 which belongs to the species *Escherichia coli*.

10. A method for ncreasng productbn of 107891 by a microorgansm capable of produdng 107891, said method comprising: transforming with the recombinant DNA vector of claim 1 a microorganism that produces 107891, wherein said DNA vector is an expression vector.

\* \* \* \* \*

SEQUENCE LISTING

<160> NUMBER OF SEQ ID NOS: 36

<210> SEQ ID NO 1
<211> LENGTH: 20000
<212> TYPE: DNA
<213> ORGANISM: Microbispora sp. PTA-5024

<400> SEQUENCE: 1

```
actcgtcgtg ctggcgtgca cgctggtgct gctggccgtg gctcggatct ggacggagcg     60
ttaccggtga acaccagcat cagcatcacc gacctgacga agcgttaccg gcgcggcggc    120
gagaggccgg ccctgaacgg ggtgagcctg accgtggacg gcgggatgac cgcgctgctc    180
ggggccaacg gcgccggcaa gacgaccctc atgcgcatct gcgtgggcgt cctgcggccg    240
gacggaggcc gcgtggtggt gggcggccac gacctcggta cggcggccgg ccggagggcg    300
gtcaagcgcg tcctgggcta cctgccgcag gagctgtcca tgtacgacga cctgaccggg    360
cgggagttcc tcgactacat cgccctgctg aagggcgtcg acgacaagcg tgtccgccgc    420
gaccagatcg agcagatgct cgagctgacc ggcctgtccg agcatgcggg ccggagactg    480
ggcggttact ccggcgggat gaagcggcgg ctgggaatcg cccaggcgct actcgccgag    540
ccggagctga tcgtcgtgga cgagcccacg gccgggctgg acccctccga acggatgcgg    600
ttccgctcct tgctggccgg cctcggcggg gcgcggcgta ccgtggtgct gtccacccac    660
atcctcgacg acgccgcgca gacctgcccc aacaccatcg tgctgcacca ggggcgggtc    720
gcctaccagg gcagcaccgc cgggctcgcc gcggtcgccg agggccgcac ctacctgctg    780
ccgcccggag cgcaggcgcc gcccgaggcc gtggtcgtga acgcggcggc ggaggtggag    840
gggacgcgct atcgcgtgat cagcgcgcga ccgccgatcg gcggcaccct catgacgccg    900
acgctcgaag acggatacgc ggcactgtta cagctcggcg aaccctcccc cacgggtccg    960
cggccatgat cttcggaccg gacttccacc gggaccccta tccggtctac cggcggctga   1020
gggacgaggc gccgtgccac cacgagccgg ccctcgggct ctacgccctg tccaggtacg   1080
aggacgtgct ggccgcgctc aggcagccgg cggtgttctc ctcggccgcc cgcgctgtgg   1140
cgagttcggc ggcgggcgcg gggccgtacc gcggagcgga taccgcgtcg ccggagcggg   1200
agaccgccgc ggagggggccg gcgcggtcgc tgctcttcct ggacccgccg gagcaccagg   1260
tgctgcggca ggcggtgtcg cgggggttca cgccccaggc ggtgctacgg cttgagccgg   1320
ccgtacggga catcgccgcc gggctggccg accggatcgc cgaccgcggc ggcggcgagt   1380
tcgtcaccga gttcgccgcc ccgctggcga tcgctgtgat cctgcgcctg ctcggcgtcc   1440
ccgaagccga ccgggcacgc gtgagcgagt tgctgtccgc ctccgccccc tccggcgccg   1500
aggccgaact gcgctcctac tggctcggcc tgagcgccct gctgcgtggc cgcgaggacg   1560
cgggcaaggg cgacggcgag gaccggggcg tggtggcgga actcgtccgg cccgatgccg   1620
gcctgaggga cgccgacgcg tcggcgggcc cggcctgccg cgcacccctg accgacgagc   1680
aggtcgccgc cttctgcgcg ctcgtcggcc aggccggcac cgagtcggtg gcgatggcgt   1740
tgtcgaacgc tctggtgctg ttcggccgcc accacgacca gtggcgcacg ctgtgcgcga   1800
ggcccgacgc gatccccgcc gccttcgagg aggtcctgag atattgggcg ccgacccagc   1860
accagggccg taccctcacc gccgatgtgc gcctgcacgg ccggctgctc ccagccggag   1920
```

```
cacacgtgct gctgctgacc ggatcggcgg gcagggacga gcgcgcctac cccgacccgg    1980
acgtcttcga catcggcagg ttccaccccg accggcgacc gagcacagcg ctcgggttcg    2040
gtctcggcgc gcacttctgc ctggggggcgg cgctcgcgcg gctgcaggcc agggtcgccc    2100
ttcgagaact gacgcgtcgc ttcccccgtt accggacgga cgaggagcgg accgtgcgat    2160
cggaggtcat gaacgggttc ggccacagcc gggtcccgtt ctccatgtga accggcgggt    2220
ggccggacgc tacgtacagg gcatgacgaa cacgaccaga gcccgcctgt ccggcgccgg    2280
tctcctcgcc gcggccctgc tgctggccgg ttgcacgggc ggcggcagag ccgatccggc    2340
gcacaggtcc cccgtgccgt tgccgagtcc cacgagcaac aagcaggaca tcagcgaggc    2400
gaacctcgcc tatctgtggc cgctcacggt cgaccacggc acgatcgagt gcctgccctc    2460
cgacaacgcc gtcttcgtgg cgcccgacgg cacgacctac gctctcaacg accgcgctga    2520
gaaggcgggg cacccccccga tcacaccgat tcgcgccaag ggcagcggtg cggatacat    2580 cagcctcggc gccctgctca gcaccaccct caatctctgc ggaaagggct gagaccagat    2640
ccgggaccac aggagacggg ccgtccggtg aggcggcggt ccgaaaactt acccgagtgt    2700
gggacggaaa atccggctcc tgcgtgaacc ttcgtgcgcc atctcgctac gtacacctcc    2760
gaaagatcga aactgccgga ggtaacaggg acaggtgcac gggggagata cgcgatgccg    2820
atggtgcgcg agtgcggtgc ggcacaaccg gccggaacgg aggcgatgtg cgcggcacgg    2880
acagggcctg tgacgggggg acgaccagcg acaccgggag ggacatcggg cacaccgggg    2940
gtgcccgacc ggcaaaggac gaggagagcg accgaggggt ccgccgacgc cggggccgc    3000 ggcgaggtcg tcgtcgcatg cgccagcctg cgcgacacga acgcgccgtt ggcggagtgg    3060 ctggagacc tggacgtcgg ctgcacgttc tgcggcgacg tctattcggc cgcggagacg    3120
tatgacccgc ggctggcctt gctgcccgtc ctcaccgagg cccaggcgca gcgcctgggc    3180
aggctgatgg agcggtgccc gggcacgtcg gtgctcggca tcgtcatgga cgtgaccggc    3240
caccatactc atcgggccat ccagaacggg gcgagctggg tgctcaacac gctgctcccg    3300
gccgcgtgct gccgcaacct gctgcgcatg tcattcagg cggtggtgct cgggcccacg    3360 gtcccccgagc cgctggtcgc cgagccggcg gttccggagg gcgcggagcc gcccacgcgg    3420
ccgggcgacc cccgtgcgga accgccggcg gaggcgcgga aggtcgccga cgcgcaggag    3480
gaggaactgc tcacgctgct gtgcgggccg gagtccatcg ccgagatcgc cagacgcttc    3540
tactgttccg aacggtcgat gtaccgtcag ctacgcgatc tgtaccgaag ttacggagtc    3600 accgacgcc gggagctccg ccgggagatc gctcttcgga gcgtcacgcg ccaccaggag    3660
acgctgtcgg cccaccttct cgccccgcct cggcccgtcc gccggggcgg tttgtcgtgc    3720
tgagggctgg cacaccgccg ggctgtggca caccacgacg ccgggttgcg gctgcagct    3780 ttggcagagc cggcagcgcg ccccggacgc cgggcgcggc gtcccgcgta gcgggccccc    3840
cgaacccgcc ccccgctccc gtcagccgtc cgacccggac agccgcgcc ggcggggccag    3900 ccagacggcc gcggccagca gtgccagagc gcacgagagc atccagggt gcgtgccgga    3960 caccacggcg ttcgttccgg tccgcgtacc catccgagca gccagaccac gactcccgcc    4020
atcgttccga aggcgggtga ccgccagatc gcgaagacgg cgcccgcgcc cgccgccagg    4080
agggcgcggc cgagccagcc ggcgacgacg gcgagcatcc ccgtagtcgc accggcggac    4140
acgaggacgc ccgaggcgac gaccgagagc gcgaggtcga ttcccaggac gagcgcgagt    4200
ctggtggcga acgccgtggc gggagagacc ggcatcgccg acagcagctc caggcgtgga    4260
tcggatcggt gtgagcacgc cgtgaccgag ccgagcagca gcaccaccgt caccaccgag    4320
```

```
ctgaacaact gcacgaccgc tcccggggtc ggcgccgtgc gcgcgagcaa caccgccgcg   4380
accaggccca gagcggtcag cgggccgagc gaccgcggta tcagccgtgc ctgcgcccgc   4440
acgagaccgg tggtcagccg ccacgacgcg cgaagcgtgg ggccggtcac gggcgccttc   4500
cggtgtccgg cgatgtccgg caggcggccg aggagctcgt cgtacgccgg gaccgtgagc   4560
ggcccgatca gttcctcgtc ggcttcgcgg accgcggccg tcagggcgtc ctgatcctcg   4620
tcatctatca ccagtccgcc ccccttcgg atttgtcgtt tttgtcagtg cctccgtcag   4680
caaccggcgg gccatgtgca tccggctctt gaccgtgccg gttggaattc caagtattac   4740
ggccacctgt ggatagggga gatcctcggc gagcacgagc acgagcacct cgcgcaggtg   4800
ctcgggcagc tccgccaccg cggccaccag gtcccgccgc tcggcgcggg cgagcacctg   4860
ctcgtcgacc gccggctcca gatcgggcac gtccgcggcc ttctccagat ccacgaggac   4920
cggttcggcc cgccgtagcc ggttgtgcgc ctgacgccgt gccaccccca gcagccaggc   4980
tcgcaccggc gcctcgcccc ggaaactgcc ggccgagcgc cacccgcca gccaggactc   5040 ctgaaggatc tcctccgcca cctcgcgctg ggaggtgagc cggcggatga gccgcagcat   5100 cccggcggc tggcgttcgt acagcatacg gagcgccacc tcctcgccgt cggccacgcg   5160
tctcatgagg acggcatcct cggacacctc cgcggagagc tccggttcac gcaactgctg   5220
cacacgttcg tatgtagcgt cggctgccgt accggttcgg ggggatctgc ggcgtagcgg   5280
cacgagtgcg ctccgtcctc gtttctgtca ttcctgccat tcattgagcc gttattgaca   5340
ctagtagtcc gaaatgttcg actcaatgcg attccggaat cttgtccgaa cgaacaccgg   5400
aaaggagcga gcaatgcccg ctgacatcct ggagacccgg acttccgaga ccgaggacct   5460
gctcgacctc gacctctcga tcggtgtcga ggagatcacc gccgggccgg cggtgacgag   5520
ctggtcgctg tgcaccccg ggtgcaccag ccccggcggc ggcagcaact gcagcttctg   5580
ctgctgacat aaccgcagac gacaggggct gtagccagcc cgggccggag cgcgtcccgc   5640
cccggtccgg gccaccggcc ggaacacgag ccggcgcggg cagggcagaa aggaccaggt   5700
ggaaaatgac agattcgcca tttcgtgcgt gggatgtctt tatggtccgg gcaccggttg   5760
gttatgcata tcctactcca ctgccgaact ccgaattcga ttctccggca tcctcacctg   5820
gccttgacga agcggagttc ccgcctgacg cgcccgttct gtccgatgtc tccggacaca   5880
gagccggctc gtccgaggcg tccgcacgca cgtccgggcc gccgccggcc gacgatcatc   5940
tctcgctgct gcgggcggcg tgcgaagacg ggccgctgat ggaggccgtg gagctggcct   6000
cacccagcct ggccggtctg ctcgccaggg tcgcgcgcgg cgacacgggc gggctcaagg   6060
acaagcggct gcgccgggcc gccctcgcgc tcctgcgcta cgacatccgg atgcgaaccc   6120
ggccgactcc gttcggcctg ttcgccgcg tcagcggcgg ccggttcgac acgtccgcga   6180
agtggctggc cgggacgggt catcgcacca ggacgcgcgc cgacatggag tggctgctgt   6240
cggcggtgca ccgctcgaa cgggatcgtg tgctgctcgc cggcgtcacg gtgcaggcgc   6300
accagaccct gaccgtgcgc ggcgaccgga tcgtccttga ctgtccttcc gctctcggca   6360
aacccctcaa cggatccacc cgttcgaccg tctccgcgcg gcgctcgccg gtggtcgccg   6420
agatccttgg cgccgcccgg cgccccgtcc tcgcgggaag gctcgcgcag agcgtggcgc   6480
agcggttcga gctgccggtc gacggggtga cgggcctcct cgcggacatg gccgcccagg   6540
aactgttgat caccgcgctg cggccgccct tggacggggg tgacccgctc cagcacgtgc   6600
tcgacgtcgt ggcgacggcg gaggcgaggg cgggttcgcc cgccgaggcg atgagctccg   6660
attcggccgc cctggtggcg gcgctgcgcg aggtggacgc gcgctgccac gcctacgatc   6720
```

-continued

| | | | | | |
|---|---|---|---|---|---|
| ggaccgccgt | cgggcagggg | cgccgggagc | tggccgagct | gatccaggcc | acgcggcggg | 6780 |
| tccacccgca | cgacactccg | ctgcacgtcg | accttcggat | cgacctggag | gtgcgactcc | 6840 |
| ccgagatcgt | gcgcacggag | atcgagcggg | cggccgaggc | gctgtggcgg | ttgtccccgc | 6900 |
| cgcggcgtgg | catgcgggcc | ctgcgccgtt | accacgaggc | gttcctggag | aggtacggcg | 6960 |
| cggaccgtgc | ggtgccgctg | ctcgaactcc | tcgacgacac | gcgcggactc | ggcccgcccg | 7020 |
| ccggctacaa | gtgccgccg | agcgagacac | cggcgggccc | gcaagaggag | cctgccgca | 7080 |
| gtgcggcgct | cgcccggctg | gtcgccacgg | cggcccggca | cggggagcgt | gagatcgtca | 7140 |
| tcgacgagga | gacgatcgcc | gaactcgtct | acgacgaggc | ggctccggcc | gatctgccga | 7200 |
| actccttgga | gctgggggtg | cacgtggtgg | ccccgtcgct | ggacgagctg | tccgccggaa | 7260 |
| ccttccgagt | cgtcctggcg | cccgggccgg | gctcgcacca | cgcgggcgcg | acgtcggca | 7320 |
| ggttcaccgg | tctgctgccc | gatgtggacg | ccgagtcggc | ggccaggcag | gccggccggc | 7380 |
| ccctgcacat | ccaggacgcg | gtcgccgccg | atgtcgcctt | cattccgcgg | tccgccgggg | 7440 |
| cggccaacct | cgcgcacacc | ccctcgtact | ccggccggcg | catcagcgtg | gggctcccgg | 7500 |
| acagcggacg | cgcgcaggaa | ctccccctcg | acgagctggg | ggtcgcggcc | aacctggaac | 7560 |
| gtctctgcct | cgtccacctg | ccgacaggcc | gtgaggtggt | ccccgcactg | ccgaacatgg | 7620 |
| tcagcgcctt | cgcgcaggcc | ccgaaccccg | ctcgcctgtt | gttcgagctg | ggcctggagg | 7680 |
| ggcagcggct | ctgggaaccg | tgggactggg | gggcgctgag | cgagatgcca | ttcctgcctg | 7740 |
| gtgtgcgtta | cggccgtacg | cttctggccg | ctccgatctg | gcggatggat | cagctccgcg | 7800 |
| ggccggccgc | cgactccggt | ccggcggcgg | actgggacgc | ggcgctcgac | cggtggcggg | 7860 |
| cggagtggaa | cgtcccccgg | cgggtgctcg | ccgtcagcat | ggaccagcgc | ctgctcctcg | 7920 |
| acctcggcga | cgcctggcac | cgcgtactgc | tccgcgacga | actgcgcagg | acacccgagc | 7980 |
| tgatcgcgca | gcaggtggcc | ggcgacgagg | agggctggct | ggaccgcggt | gacggggct | 8040 |
| ttcccgggca | cctcgccgag | atcgtggttc | cgctggaacg | ccgtgaccgc | cacgccgccc | 8100 |
| ggcctccgca | catcagggcc | accgtcggcg | gccgcgagcc | gaccggagcg | gggggaccgt | 8160 |
| ggctctacct | caggctgcgg | gtcccgcgcc | ggaaccagga | cgacttcctg | cgcgaccagg | 8220 |
| tgcccgtcct | ggtacgggcg | gggatcgggc | acggcgccga | ccgctggttc | ttcatccgct | 8280 |
| acagcgacac | cgccggacag | cacctgcggg | tcaggttccg | cggcgagcgg | gagaaactgt | 8340 |
| gggccgggct | gctccccgag | atcggcgcgc | ggctcgtcga | gtggcagcgg | caggggctgc | 8400 |
| tggcgggcca | cgagctcggc | cagtacgacc | ccgagtacga | gcgatacggc | ggcgacgcgc | 8460 |
| tggccgagtt | caccgaggcc | gccttccagc | acgacagcgc | cgcggccatc | tcgctcctgc | 8520 |
| gcctcaccag | gcgcgccggg | ttccgctaca | cgctcgacga | ggtgacggcg | atctcggccg | 8580 |
| cggcgctggc | gcacgccttc | ggtcctcccg | ccccggtcgt | cgagccggtg | ccgctggtgg | 8640 |
| gcggcctcca | gtgggctccg | gatctgttcg | acggcgaccc | ggccgccgcg | tggatgagca | 8700 |
| ccaccggagc | ccgcagggaa | ctaccgcccg | actaccggcg | tgagccggcc | cggtggcaga | 8760 |
| agctgatcga | ccccaccgga | ggctggcggg | tgctgcgggc | ggatgaggac | ggctgtcagg | 8820 |
| tgctggcagc | cctggaatcc | agggatgagg | ccgtccggcg | gttcgggact | gccttccgcg | 8880 |
| aggcgtccag | acccacggac | tccccgtcga | cgcagctcag | actggtcggc | agcctgcttc | 8940 |
| acatgacctg | caaccggctg | atcggcggat | ccgcggaacg | agagcgaagc | gtgctcgggc | 9000 |
| tcgcccgggg | cgccgtccag | gacaacctga | accgcaggag | gcaccgggca | tgaccacagt | 9060 |
| cggtccgaca | tcgtgcgggg | tgaccctga | ccggcacccg | gcccggttcc | tgcgcggcag | 9120 |

```
cgcggcccgc cgggccgcgc gcctggtgcg gctggtcgcc gaacggctcg ccgacccgga      9180
cgaggtcgcc gggatcgcgg cccgcccegg caactccgtg ccggcgaacg ggctgtcgat      9240
gtggagcccg gccacgctgt cgcacggatt tccgggcatc gcggtcttct acgcggagct      9300
ggggcgggtc gaccccgcct ggtcggcgtt ggcacatcgc cacctcaggg cggggccgc       9360
ggctgtggag acggcgcctt cgggcggact gttcgccggt ccggcctctc tcctggccgc      9420
cgcgcagagc tgcgcaggcc cggcggggca ctaccggggc ctgcgacgca cgctgaccgc      9480
atggctcgcc gctgatcacg ccggacggct cgccgccgcg cgtgaccggc ccggccccgg      9540
tgtcgcctgg accgactacg acgtcgttca cggactgtcc gggtccaccc gtctgctgct      9600
ggacgccgcg cgcgatcccg acgacgagac ggcggcaaag gcctccggcg cggtgaccga      9660
caccctgcgg cacctggtgc ggctcaccga gccgatcaca gtggacggac acgaggttcc      9720
cggctggtgg gtgccgtccc atctgcagcc ggtcgaacag gaccggcgcg actaccccg       9780
gggagacctg aacctgggat tggcccatga agcggcgggg ccgctgtcgg tgctggccac      9840
ggccacccctt cacggggtgg aggtcccggg ccagcgtgag gccgtcgcgc ggctggccga     9900
atggctgctg ggctgaacga tgaccgacga cacgggcgcc tactggccct gccgggtcag     9960
ctgggacgag cagatcgccg ccgtccgccc ggacacctcc ttcacccgta cggcctggtg    10020
ctacggggcc cccggagtct cgcggcact ccaccgggcc ggactggcgc tcggcgtgac     10080
ggagtggcgc gaagtcgcgg tcaccgcgct gctggacggg ctgcgccgcg accggtccgc    10140
ctggcgggtg gacggctcga ccgtctgtca cgggtacgcg ggcctgctgc aggtgctgtc     10200
gcgggtcggc gccgagtccg gcgacccgcg gctgctggac ggctgcctgg acgtcgcgcg    10260
catggtcctc ggcgaggccg acgaatcggc tccgttcgtc ttccccccatc tcgtcccga    10320
ttcgcccgac gggtggcgca acgccacggg atacctgccg ctggacggcg ccggcttgct    10380
ggaaggggcg gccggagtcg cctgtgcgct gctctcggtc atcccgccgt cgtcgctcgg    10440
tggaacggac ccggccccgg agcgtgcgga cctcccgccc tgggacaggt gcctggccct    10500
gtgctgacgc ccccgaccca tcaggagagc cagaccatga cagcgcacag cgacgcgggc    10560
ggcgttccgc ggccccgga gcggctgctg ctcggcgtga cggctcggt cgccgcgctg       10620
aacctgcccg cctacgtcta cgcgttccgg gccgcggcg tcgcccggct ggccgtcgtc     10680
ctgacccgg cggccgaggg tttcctgccc gcgggcgcgc tgcgccgat cgtcgacgcc      10740
gtccacacgg agcacgacca gggaaagggg cacgtggcgc tgtcccgatg ggcgcagcac     10800
ctgctcgtcc tgcccgcgac ggcgaacctg ctcggttgcg cggcgtcggg gctggcgccg    10860
aacttcctgg cgacagtgct gctggcggcc gactgcccga tcacgttcgt gcccgcgatg    10920
aaccccggtga tgtggcgcaa gcccgccgta cggcggaacg tcgccaccct ccgcgcggac   10980
ggtcaccgtg tggtggaccc gctgcctggc gcggtgtacg aggcggcctc gcggtcgatc    11040
gtcgacggac tgaccatgcc tcggccgag gcgctggtcc ggttgctggg cggcggggac     11100
gacggcagcc cgtccggtca ggacggtccg gtcggcaggg cggagcacgc ggagcacgcg    11160
gaggccgcgg aggccttggc atgacggtcc cggcgttcga gctcagcgac ctgacggtcc    11220
gctacggccc ggtcacggcg gtcgacggcg tctcggccgg ttcggcgccc ggcctcgtca    11280
ccgccctgct cggacccaac ggtgcgggca agtccagcct gctccgggtg ctgtcgacgg    11340
tcgcgccgcc ctcatcgggc acggcgaggg tgttcggcca cgacacgcgc gcggagccgc    11400
tggccgcacg taggcggatc gggctggtct tccaggaacg cgcgctcgac accgacctgt    11460
ccgcggagca gaacctgcgc tttcacgcgc ggctgttcgg ggtggggcgg gcccgggccg    11520
```

```
cggaggacat cctcgtgctg ctggaacgct tcgggctggc cggccgcggc cgcgaccggg   11580
tcgagaccct ctccggcggg ctggcccgcc ggctggagat cgcgcgggcg ctgttgcacc   11640
ggcccggcct gctgatcctg gacgagccga ccaacggcct cgaccgggag gcgcgccaga   11700
ccgtatggga cgacctcatc cggctgcgct ccgaactcgg cgtcacggtg ctgtactcca   11760
cgcactacat ggacgaggcc gagctggccg accagatcat catcctcagc gagggccgcg   11820
tcgcggggtt cggctcgccc ggccggctga agagcgagct gcgatcgtcg cgcatcgtgc   11880
tcgtcaccca cgacgacgac acggtgctcg cccggctcgc ggaggccggc ttcgacgctg   11940
tgatcgactc ggacgcgtc gccgtgcgct ccgcgaacc ggagagccgg atggcggagg   12000
tcatacgggc ggcgggggccg ctcgtccgcg cggcgtccgt gcaccacccc tcgatgaacg   12060
acgtgttcct ggcccacacg gccgcgaacc gcgacaggga ggcggccgat ggcactgtca   12120
gctgtccgtg acaccggtgg cacggcgggg agtactcccg gcggccccgc cggaggcggg   12180
tcggccggcg cgggcgaggc gaggaggctc gtctctgcgg ccctgcggtc cggggtccgc   12240
ggaacgctcg tcgtggcgca ccgcgacgtg ctgcggcagg tgcggcaccc gggggtcgtg   12300
gtcgcccagg ccgcgcagat cgtcttttc gtcctcgtct acgccgtggg cttccggtcg   12360
atgatcggat ccgtcggcgg cgtgtcgttc ggcgcctacg tctatccggg gatcatcgcc   12420
atccaggtcg tcatgctggg cgtcggcacg ggcctgacgt acgcgatgga ccgcgagttc   12480
ggcgtgctgc gcgagatgca ggtcgcgccc gtgccacgca tgtgcctgcc cctcggaaag   12540
atccttgcga gctgcgtgct gctcaccgcg caggccatgc tcatgctcct gcccgccccg   12600
ctgctcgggc tgcccctgac gcccgcgcga tacgcggcgg gcgccgcggt ctacctggcc   12660
acggcggcgg ccttcagctt gatcggcctg ctgctcgcgg tgagcgtccg ccggatcgag   12720
acgctgcagg cgaccgtcca gctcgcgatg tacccgctgc tgttcctgtc gggttcggtg   12780
ttcaaacccg acgccgtgcc cggctggctg gcggccctca tgcggctcaa cccgatgacg   12840
tacgcggtcg atctggcgcg gcacgtgctg ctgccgtcgg ccccgggcgt gtcgtacctg   12900
cccgtctggc gggacctcct ggtgatcgcc gcgctggtgg cggccgcgtc ggcggcgctg   12960
cggctgcggg tggggaggtg accggccggt gaccaccgcg acgacgacag ggccgaccgg   13020
ccgcgagacg ctgcttgaag gcgcggtgtc ctggctcgcg gcacgactgc gctggttcga   13080
ccccgagcag tgggcgaggc atctgcagcc gagaggcttc gcgccgagcg cgctgctgga   13140
actccttatc atctgccgca acctgaactc ggtctacggc cctccgcgcc cgccggaccc   13200
ggaggacggc tcccgcgggt ccggcgtacg ggcgacgggt gcggccggcc cggccgtcga   13260
actgagcggg cgtgcgctgg acctggccga ggaggtcgtg ggacggcccg atttcggcgc   13320
ggccctctac cgcggcgacg ccgccttccc caccacgtgt ggctggtcgc gcttctcgcg   13380
gagggcggcc ggtccgtcga ccgtggcct gccgtcgccc agcggatcat cgacgcgggc   13440
tgcgccgagc cgatccggcc gggacggccg acggcggccc ggctggaggc ccgctacgtc   13500
ttcgacctcg ccggcctccg ccacgggctg cccgccatgg gcgaactggc cggtcgtacg   13560
gctctgggcc ccggtgcgga cccgctgcac ctcaccgacg cggacctcta tgtgatcacg   13620
cacatgctct tctacctcac cgacttcggg cggcgcccgt tctccgcgga cgaggccgaa   13680
agccggcggg tccgcgggct cgtcgaggtg ctcctcggcc gccagctcgc ggtcggcgac   13740
ctcgatctgg cggccgagct gctcgcctgc gcgggcctca ccggcgccga cgaccggctg   13800
tccggctgcg cgtggaaccg gttgtcggcc gcgcgccgtc cggacggctc ggtgcccagc   13860
ccgctgttcc ggcaagccgc gctggaccgg ctgagcgggg agaaggccga ggcgtacgcg   13920
```

```
ttcggaacct gctaccacac caccctcgcc atggtgctcg cggcgacgct gacggacggc    13980
gccgatggct gacccgttgc tgaccggggc cctcgcacgc gtcgtgccgg cgctggagaa    14040
gctggacggc gagcgcgccg cggcggtgct cctgctgtgc cgggcggctc tcgacggccc    14100
atcgcggccc aggccgggcg gccgccggcc tgaagcgccg ccggttcccg gatcggtgga    14160
cccggctttc cgacctgctc cacgacgctc ccggaaccgc gcagggcctc gccgggcaga    14220
tcgccgagac gaccgctttc ggggccgtcc ggcccgccgc cgccgtccgg gaggtctggg    14280
agctcgccgt gcccgcgctg ctggccgccg ccgcgcgcag ggccgacctg atgaccctgg    14340
ctccgctcgt ccgggccggc gtcttcctcc aggcggtctc gtccgccggc gacgtgcccg    14400
agcgggacga ccggcccgct cctgcgggcc tgaccacgcg cgccgcgtgg cgcctggcgg    14460
cgtggcagcg tccggacggc gggttcgggg cgccggccgc gaccgccgac tgtggctggg    14520
cgctcgcgga ggccgcggtt cccgggctga ccgcctcgca gcgcgagttc gccgtgcccc    14580
tcccggacgg gaagcctccg gcacggccgc gaaccgccca ctccccaccc gctacgtacg    14640
gcgggaagga gtgatgcaga tgaacgacca tgacgcggcc ggcgtcccgt ccggcagccc    14700
ggcccaccac cgaccggcgg accccgccgc caccctggcc gcggagacca caggggccc    14760 aggcgggacc gccggcccga ccgactcccc gtcgatggcg gccctgatat ccacggagtt    14820
gctcagactg cgttccggct tcgtcggctg gtacatcctg ctgtcgccga tcgtgatcgc    14880
cattccgctc tacctggggt cgatcttctc cccggagggc cggtccggcc gcctctggga    14940
gaccttcagc aacgtgacgc tggagttctg gggcgtactg attccgatga cggccggtct    15000
gatcgcggcc ctcgcggtcc gtgccgacac cgaaccctgg cgtttcctgt tctcgtacgc    15060
gatcccacgc tggcgctact tcaccgcgaa ggtcgccgcg ctggccgtcg cccagttgct    15120
gtcggcgacc atcctggtcg tgatgctggc cgggggagcc ctgctgaccg ggcagctctc    15180
caacgccgcc tcgatgatcc tcaaagtcgc ctacctgccg tgggcggcgg ggttggcggc    15240
gaccgcgctc gccgtcctcg tctgcaccgt ctggggactg gccccggca tcgcccttgg    15300 tgtggccggg atgatggcag gcgcgctcat ctccgacaag tcgttctggt acgccatccc    15360
gcccgcctgg ccgatgcggg tcatcctccc gctggcggac atccgcccca acggcctggc    15420
gctcgacgcg agcagcccgc tccacgacac ctcggtcatc ccgctggccg tcgcgctctc    15480
ggcccgcggc acgatcgtga tcctgctgat cggcggccgg cacatggcgc ggaaggaggt    15540
ctgacatggc cgctctcgag atcagggacc tgcacaagca ctacgacgac ttccacgcgc    15600
tcgacggcgc gaacctgacc gtgccggacg gctccctcta cggcctgctc ggcccgaacg    15660
gcgcgggcaa gaccaccctg atgaaggcgg tcaccgggct gcggcatccg acctcgggcc    15720
acatcagcct tttcggcggg ccctacgaac ggcggctgct gacccaggtc ggcgcgctgc    15780
tcgagtcgcc gggcctgtgg acccagctcg acgcggtgtc ccacctgcgc atccacgccc    15840
ggctgcgcgc cgtgcccgag acacggatcg gcgaggtgct gagcctgatg aacctcaccg    15900
aggtcagcac ccgcaaggtg gcgaagtact ccctcggcat gcggtggcgt ctcggcatcg    15960
ccatcgccct gctcggccgg ccccggctgg tcgtgctcga cgagccgatg aacgactcg    16020 acccggtcgg catcagggac atgcgggcga cgctgcgcgc gctgaccgcc gccgggacca    16080
ccgtcatggt ctccagtcac cagctggcgg agatcgcgca catctgcgat cacgtcggcg    16140
tgctggtggc cgggcggacc gcgtacgagg gcccgctgcc cggcctcgcc gtggacggcg    16200
acctcgaaca gggcttcttc cgcctgctcg agaaggcggg ttccgcagtg agatgacctg    16260
acccacgaac ggaagggcga tcgggaacat ggcgaggtcc gaagagagca acaccctggc    16320
```

```
caggctgttc gacgtgctcg gcgacgacgc cgcggcggcg agggaatggg tgaccgagcc      16380
gcaccggctc atcgcctcga acgagaggct cggcaccgcc ccggaagcgc cggccgacga      16440
cgaccccggg gcgatccgca cggtgggagt gatcggcggc ggcaccgccg gttacctcac      16500
cgcgctggca ctcaaggcca agcgcccctg gttggatgtg gctctcgtcg agtccgccga      16560
catccccatc atcggcgtcg gcgaggcgac ggtctcgtac atggtgatgt tcctgcatca      16620
ctacctcggc atcgacccgg cggagttcta ccagcacgta cgccccacgt ggaagctcgg      16680
catcaggttc gagtggggca gccggccgga gggattcgtc gcgccgttcg actggggac      16740
cggctctgtg ggactggtcg gctcgctgcg cgagacgggg aacgtcaacg aggccaccct      16800
gcaggccatg ctgatgaccg aggaccgcgt ccccgtctac cggggggagg gcgggcacgt      16860
ctccttgatg aagtacctgc ccttcgccta ccacatggac aacgcgcgcc tcgtccgcta      16920
tctcaccgag ctggcggctc ggcgcggcgt cgccatgtg gacgcgacgg tcgccgaggt      16980
acggctcgac ggcccggacc acgtcggcgg cctgatcacc accgacgcc ggcggctgca      17040
ctacgacttc tacgtcgact gcacgggctt ccgctccctg ctgctggaga aggcgctggg      17100
catcccgttc gagagctacg cgagcagcct gttcaccgac gccgccgtca ccggcactct      17160
cgcgcacggc ggccacctca agccgtacac gacggcgacc acgatgaacg cggggtggtg      17220
ctggacgatc ccgacgcccg agagcgacca tctcggctac gtgttctcgt cggcggcgat      17280
cgatcccgac gacgcggcgg cggagatggc gcgccgattc ccgggggtca ccagggaggc      17340
gctcgtccgg ttccggtccg gacggcaccg ggaggcctgg cgcggcaacg tcatggcggt      17400
cggcaactcc tacgcgttcg tggagccgct ggagtccagc ggtctgctga tgatcgccac      17460
ggcggtgcag atcctggtga gtctgcttcc ctcctcccgc cgggacccgc tgcccagcga      17520
cgccgccaac caggccctgg cacaccgctg ggacgcgatc cgctggttcc tctcgatcca      17580
ctaccggttc aacggacggt tggacacccc gttctggaag gaggccaggg ccagaccga      17640
catctccggg atcgagccgc tcctgcggct gttcgcggcc ggagcgccgc tgaccggccg      17700
cgactccttc acccgatacc tcgcggacgg ggcggcgccg ctgttctacg gtcttgaggg      17760
cgtcgacacg ctgctgctcg ggcaggaggt gccggcccgg ctgctgccac ccgcgagcc      17820
cccggagcag tggagggcac gggcggcggc ggccagaagc ctggcctcgc ggggctgcg      17880
gcagagcgag cgcgctggacg cctacgccgc cgacccgtgc ctcaacgccg aactgctcag      17940
cgactccgac agctgggcgg gcgagcgggt cgccgtccgg gccggcctga gatgacgacc      18000
ggcgccacgg tcgcccatgt cgtcgaaccg gacgggttcc gggcggtcat ggccacccct      18060
ccggcagccg tggcgatcgt caccgccgcg gccgcggacg ggaggccctg ggggatgacc      18120
tgcagttcgg tctgcagtgt gaccctgacg ccgccgaccc tgctggtctg cctgcggacg      18180
gcgagcccca ctctcgcggc cgtcgtctcc ggccgggcgt tctcggtgaa cctgctgtgc      18240
gcccggtcgt acccgtcgc ggagctgttc gcctcggcgg cggccgaccg cttcgaccgg      18300
gtccgctggc ggcggcccac cggtacgggc ggccccacc tggccgacga cgcccgtgcc      18360
gtcctcgact gccggctctc ggagtccgcc gaggtgggag accacatggt ggtcttcggc      18420
gaagtgaggg cgatccgcag gctgtccgac gagccgccgc tgatgtacgg ctaccgccgc      18480
tacgccccct ggcccgccga ccggggaccg ggagcggtgg gggggtgaac gccgagcagc      18540
tcaccggtgt ggtcatcgcc gatctcgggg tgatcgtcgt cgtgtcggcg ctcttcgggg      18600
cactggcacg gcgatgcggc cacccgaccg tcatcggcca gatcgtcgcc gggatcgcgc      18660
tgggaccgac cctgctgggc cggctgcccg gcgacccggc cgggtggctg ttccccgccc      18720
```

```
aggtccggcc gtcgctgtcg gtcctgtccc agatcgccgt cgtgatcttc atgttcgcgg    18780
tgggttacga ggtcgacctg cggcttctgc gccggggtgg ccgcagcgcg ctctgcgtgc    18840
cgtcgctgtc gctggcggtg cccatgacgc tcggcgcggc ggtcgccgtg ctgttccgcg    18900
aggttttcac ggtcggctcc cctgggggc cgggaggccc gacgttcgtg ctgttcatgg     18960
ccgtggcgat ctcgatcacc gccctgccgg tgctggcggc gatcgtacgg gagcggggcc    19020
tcgcgggaac cgcggcggga accgtggcca cggcggccgc cgggctgatg acgtggccg     19080
catggaccac actggccgcg gttctggccg agaccggcga tgccgatgag ccgacggtgt    19140
cacacgtgcc ctggatgctg gctcttccgg ccctcacggc gttcgcggtg ccatgttcc     19200
tggtcgtgcg tccccttctc gggtggttga ccaggaggcc cggagccatg tggggcggc     19260
tgccggcggc gttcgcactg gcgctcggca gcgcctgggg caccgccgca cttggcctgc    19320
acccggtgtt cggcggtctg ctggccgggc tcgtcatgcc gcgccgcgac ggcgcccccg    19380
agccggaggt gctgcggccg atggagcaga ccgccgagtt gctcctgccg ctgttcttcg    19440
tgatgaccgg gctgtcggcc gacatatcgg cgatcgaacc gggtgggctg atcctgctgg    19500
cggtgctcct ggtcgccgcc atcggggca agctcgtgcc cgcctacgcg gcctcccggc     19560
tgaccggtct cgactccggt gagtcggccg tggtcgccgt gctggtgaac acccggggcc    19620
tcaccgagct gatcgtgctc gatgtggggc tgtcggcgca cgtcatcgat gagcggctgt    19680
tcaccgtcct ggtcgtcatg gccctgatca ccacggccat gaccgcgcca ctgctgaccg    19740
cgctgagacg gcgcgaagag cggagacgcg gtcgtcaggc ggccccgctg tcgagggcga    19800
cggcctggcg gatgtagtcg cgcagggcgt cccggtcgag ggcgcccagg ttcttgatct    19860
tgacgtgcct cgtcgtcttg cccacgcccct ccagcaggcc gtgcccgtcg tcgaactccg   19920
cccccccggc gaaggcgaag gtgacgtgcg ttttgctgtg gctgatgatg gcgaggatct    19980
tgtcgccctt ccaggcgggc                                                20000
```

```
<210> SEQ ID NO 2
<211> LENGTH: 300
<212> TYPE: PRT
<213> ORGANISM: Microbispora sp. PTA-5024

<400> SEQUENCE: 2
```

Val Asn Thr Ser Ile Ser Ile Thr Asp Leu Thr Lys Arg Tyr Arg Arg
1               5                   10                  15

Gly Gly Glu Arg Pro Ala Leu Asn Gly Val Ser Leu Thr Val Asp Gly
            20                  25                  30

Gly Met Thr Ala Leu Leu Gly Ala Asn Gly Ala Gly Lys Thr Thr Leu
        35                  40                  45

Met Arg Ile Cys Val Gly Val Leu Arg Pro Asp Gly Gly Arg Val Val
    50                  55                  60

Val Gly Gly His Asp Leu Gly Thr Ala Ala Gly Arg Arg Ala Val Lys
65                  70                  75                  80

Arg Val Leu Gly Tyr Leu Pro Gln Glu Leu Ser Met Tyr Asp Asp Leu
                85                  90                  95

Thr Gly Arg Glu Phe Leu Asp Tyr Ile Ala Leu Leu Lys Gly Val Asp
            100                 105                 110

Asp Lys Arg Val Arg Arg Asp Gln Ile Glu Gln Met Leu Glu Leu Thr
        115                 120                 125

Gly Leu Ser Glu His Ala Gly Arg Arg Leu Gly Gly Tyr Ser Gly Gly
    130                 135                 140

Met Lys Arg Arg Leu Gly Ile Ala Gln Ala Leu Leu Ala Glu Pro Glu

```
            145                 150                 155                 160
Leu Ile Val Val Asp Glu Pro Thr Ala Gly Leu Asp Pro Ser Glu Arg
                165                 170                 175

Met Arg Phe Arg Ser Leu Leu Ala Gly Leu Gly Gly Ala Arg Arg Thr
            180                 185                 190

Val Val Leu Ser Thr His Ile Leu Asp Asp Ala Ala Gln Thr Cys Pro
                195                 200                 205

Asn Thr Ile Val Leu His Gln Gly Arg Val Ala Tyr Gln Gly Ser Thr
            210                 215                 220

Ala Gly Leu Ala Ala Val Ala Glu Gly Arg Thr Tyr Leu Leu Pro Pro
225                 230                 235                 240

Gly Ala Gln Ala Pro Pro Glu Ala Val Val Asn Ala Ala Ala Glu
                245                 250                 255

Val Glu Gly Thr Arg Tyr Arg Val Ile Ser Ala Arg Pro Pro Ile Gly
            260                 265                 270

Gly Thr Leu Met Thr Pro Thr Leu Glu Asp Gly Tyr Ala Ala Leu Leu
                275                 280                 285

Gln Leu Gly Glu Pro Ser Pro Thr Gly Pro Arg Pro
            290                 295                 300

<210> SEQ ID NO 3
<211> LENGTH: 414
<212> TYPE: PRT
<213> ORGANISM: Microbispora sp. PTA-5024

<400> SEQUENCE: 3

Met Ile Phe Gly Pro Asp Phe His Arg Asp Pro Tyr Pro Val Tyr Arg
1               5                   10                  15

Arg Leu Arg Asp Glu Ala Pro Cys His His Glu Pro Ala Leu Gly Leu
                20                  25                  30

Tyr Ala Leu Ser Arg Tyr Glu Asp Val Leu Ala Ala Leu Arg Gln Pro
            35                  40                  45

Ala Val Phe Ser Ser Ala Ala Arg Ala Val Ala Ser Ser Ala Ala Gly
        50                  55                  60

Ala Gly Pro Tyr Arg Gly Ala Asp Thr Ala Ser Pro Glu Arg Glu Thr
65                  70                  75                  80

Ala Ala Glu Gly Pro Ala Arg Ser Leu Leu Phe Leu Asp Pro Pro Glu
                85                  90                  95

His Gln Val Leu Arg Gln Ala Val Ser Arg Gly Phe Thr Pro Gln Ala
            100                 105                 110

Val Leu Arg Leu Glu Pro Ala Val Arg Asp Ile Ala Ala Gly Leu Ala
        115                 120                 125

Asp Arg Ile Ala Asp Arg Gly Gly Gly Glu Phe Val Thr Glu Phe Ala
    130                 135                 140

Ala Pro Leu Ala Ile Ala Val Ile Leu Arg Leu Leu Gly Val Pro Glu
145                 150                 155                 160

Ala Asp Arg Ala Arg Val Ser Glu Leu Leu Ser Ala Ser Ala Pro Ser
                165                 170                 175

Gly Ala Glu Ala Glu Leu Arg Ser Tyr Trp Leu Gly Leu Ser Ala Leu
            180                 185                 190

Leu Arg Gly Arg Glu Asp Ala Gly Lys Gly Asp Gly Glu Asp Arg Gly
        195                 200                 205

Val Val Ala Glu Leu Val Arg Pro Asp Ala Gly Leu Arg Asp Ala Asp
    210                 215                 220

Ala Ser Ala Gly Pro Ala Cys Arg Ala Pro Leu Thr Asp Glu Gln Val
```

```
            225                 230                 235                 240
Ala Ala Phe Cys Ala Leu Val Gly Gln Ala Gly Thr Glu Ser Val Ala
                245                 250                 255

Met Ala Leu Ser Asn Ala Leu Val Leu Phe Gly Arg His His Asp Gln
                260                 265                 270

Trp Arg Thr Leu Cys Ala Arg Pro Asp Ala Ile Pro Ala Ala Phe Glu
                275                 280                 285

Glu Val Leu Arg Tyr Trp Ala Pro Thr Gln His Gln Gly Arg Thr Leu
                290                 295                 300

Thr Ala Asp Val Arg Leu His Gly Arg Leu Leu Pro Ala Gly Ala His
305                 310                 315                 320

Val Leu Leu Leu Thr Gly Ser Ala Gly Arg Asp Glu Arg Ala Tyr Pro
                325                 330                 335

Asp Pro Asp Val Phe Asp Ile Gly Arg Phe His Pro Asp Arg Arg Pro
                340                 345                 350

Ser Thr Ala Leu Gly Phe Gly Leu Gly Ala His Phe Cys Leu Gly Ala
                355                 360                 365

Ala Leu Ala Arg Leu Gln Ala Arg Val Ala Leu Arg Glu Leu Thr Arg
                370                 375                 380

Arg Phe Pro Arg Tyr Arg Thr Asp Glu Glu Arg Thr Val Arg Ser Glu
385                 390                 395                 400

Val Met Asn Gly Phe Gly His Ser Arg Val Pro Phe Ser Met
                405                 410

<210> SEQ ID NO 4
<211> LENGTH: 260
<212> TYPE: PRT
<213> ORGANISM: Microbispora sp. PTA-5024

<400> SEQUENCE: 4

Val Pro Asp Arg Gln Arg Thr Arg Arg Ala Thr Glu Gly Ser Ala Asp
1               5                   10                  15

Ala Arg Gly Arg Gly Glu Val Val Ala Cys Ala Ser Leu Arg Asp
                20                  25                  30

Thr Asn Ala Pro Leu Ala Glu Trp Leu Gly Asp Leu Asp Val Gly Cys
                35                  40                  45

Thr Phe Cys Gly Asp Val Tyr Ser Ala Ala Glu Thr Tyr Asp Pro Arg
            50                  55                  60

Leu Ala Leu Leu Pro Val Leu Thr Glu Ala Gln Ala Gln Arg Leu Gly
65                  70                  75                  80

Arg Leu Met Glu Arg Cys Pro Gly Thr Ser Val Leu Gly Ile Val Met
                85                  90                  95

Asp Val Thr Gly His His Thr His Arg Ala Ile Gln Asn Gly Ala Ser
                100                 105                 110

Trp Val Leu Asn Thr Leu Leu Pro Ala Ala Cys Cys Arg Asn Leu Leu
            115                 120                 125

Arg Met Val Ile Gln Ala Val Val Leu Gly Pro Thr Val Pro Glu Pro
130                 135                 140

Leu Val Ala Glu Pro Ala Val Pro Glu Gly Ala Glu Pro Pro Thr Arg
145                 150                 155                 160

Pro Gly Asp Pro Arg Ala Glu Pro Pro Ala Glu Ala Arg Lys Val Ala
                165                 170                 175

Asp Ala Gln Glu Glu Glu Leu Leu Thr Leu Leu Cys Gly Pro Glu Ser
                180                 185                 190

Ile Ala Glu Ile Ala Arg Arg Phe Tyr Cys Ser Glu Arg Ser Met Tyr
```

```
                195                 200                 205
Arg Gln Leu Arg Asp Leu Tyr Arg Ser Tyr Gly Val Thr Gly Arg Arg
    210                 215                 220

Glu Leu Arg Arg Glu Ile Ala Leu Arg Ser Val Thr Arg His Gln Glu
225                 230                 235                 240

Thr Leu Ser Ala His Leu Leu Ala Pro Pro Arg Pro Val Arg Arg Gly
                245                 250                 255

Gly Leu Ser Cys
        260

<210> SEQ ID NO 5
<211> LENGTH: 221
<212> TYPE: PRT
<213> ORGANISM: Microbispora sp. PTA-5024

<400> SEQUENCE: 5

Val Arg Ala Gly His His Gly Val Arg Ser Gly Pro Arg Thr His Pro
1               5                   10                  15

Ser Ser Gln Thr Thr Thr Pro Ala Ile Val Pro Lys Ala Gly Asp Arg
            20                  25                  30

Gln Ile Ala Lys Thr Ala Pro Ala Pro Ala Ala Arg Arg Ala Arg Pro
        35                  40                  45

Ser Gln Pro Ala Thr Thr Ala Ser Ile Pro Val Ala Pro Ala Asp
    50                  55                  60

Thr Arg Thr Pro Glu Ala Thr Thr Glu Ser Ala Arg Ser Ile Pro Arg
65                  70                  75                  80

Thr Ser Ala Ser Leu Val Ala Asn Ala Val Ala Gly Glu Thr Gly Ile
                85                  90                  95

Ala Asp Ser Ser Ser Arg Arg Gly Ser Asp Arg Cys Glu His Ala Val
            100                 105                 110

Thr Glu Pro Ser Ser Ser Thr Thr Val Thr Thr Glu Leu Asn Asn Cys
        115                 120                 125

Thr Thr Ala Pro Gly Val Gly Ala Val Arg Ala Ser Asn Thr Ala Ala
    130                 135                 140

Thr Arg Pro Arg Ala Val Ser Gly Pro Ser Asp Arg Gly Ile Ser Arg
145                 150                 155                 160

Ala Cys Ala Arg Thr Arg Pro Val Val Ser Arg His Asp Ala Arg Ser
                165                 170                 175

Val Gly Pro Val Thr Gly Ala Phe Arg Cys Pro Ala Met Ser Gly Arg
            180                 185                 190

Arg Pro Arg Ser Ser Ser Tyr Ala Gly Thr Val Ser Gly Pro Ile Ser
        195                 200                 205

Ser Ser Ser Ala Ser Arg Thr Ala Ala Val Arg Ala Ser
    210                 215                 220

<210> SEQ ID NO 6
<211> LENGTH: 220
<212> TYPE: PRT
<213> ORGANISM: Microbispora sp. PTA-5024

<400> SEQUENCE: 6

Val Pro Leu Arg Arg Arg Ser Pro Arg Thr Gly Thr Ala Ala Asp Ala
1               5                   10                  15

Thr Tyr Glu Arg Val Gln Gln Leu Arg Glu Pro Glu Leu Ser Ala Glu
            20                  25                  30

Val Ser Glu Asp Ala Val Leu Met Arg Arg Val Ala Asp Gly Glu Glu
        35                  40                  45
```

```
Val Ala Leu Arg Met Leu Tyr Glu Arg His Ala Gly Met Leu Arg
    50                  55                  60

Leu Ile Arg Arg Leu Thr Ser Gln Arg Glu Val Ala Glu Ile Leu
65                  70                  75                  80

Gln Glu Ser Trp Leu Ala Val Trp Arg Ser Ala Gly Ser Phe Arg Gly
                85                  90                  95

Glu Ala Pro Val Arg Ala Trp Leu Leu Gly Val Ala Arg Arg Gln Ala
            100                 105                 110

His Asn Arg Leu Arg Arg Ala Glu Pro Val Leu Val Asp Leu Glu Lys
            115                 120                 125

Ala Ala Asp Val Pro Asp Leu Glu Pro Ala Val Asp Glu Gln Val Leu
130                 135                 140

Ala Arg Ala Glu Arg Arg Asp Leu Val Ala Ala Val Ala Glu Leu Pro
145                 150                 155                 160

Glu His Leu Arg Glu Val Leu Val Leu Val Leu Ala Glu Asp Leu Pro
                165                 170                 175

Tyr Pro Gln Val Ala Val Ile Leu Gly Ile Pro Thr Gly Thr Val Lys
            180                 185                 190

Ser Arg Met His Met Ala Arg Leu Leu Thr Glu Ala Leu Thr Lys
            195                 200                 205

Thr Thr Asn Pro Lys Gly Gly Arg Thr Gly Asp Arg
210                 215                 220

<210> SEQ ID NO 7
<211> LENGTH: 57
<212> TYPE: PRT
<213> ORGANISM: Microbispora sp. PTA-5024

<400> SEQUENCE: 7

Met Pro Ala Asp Ile Leu Glu Thr Arg Thr Ser Glu Thr Glu Asp Leu
1               5                   10                  15

Leu Asp Leu Asp Leu Ser Ile Gly Val Glu Glu Ile Thr Ala Gly Pro
                20                  25                  30

Ala Val Thr Ser Trp Ser Leu Cys Thr Pro Gly Cys Thr Ser Pro Gly
            35                  40                  45

Gly Gly Ser Asn Cys Ser Phe Cys Cys
        50                  55

<210> SEQ ID NO 8
<211> LENGTH: 1115
<212> TYPE: PRT
<213> ORGANISM: Microbispora sp. PTA-5024

<400> SEQUENCE: 8

Met Thr Asp Ser Pro Phe Arg Ala Trp Asp Val Phe Met Val Arg Ala
1               5                   10                  15

Pro Val Gly Tyr Ala Tyr Pro Thr Pro Leu Pro Asn Ser Glu Phe Asp
                20                  25                  30

Ser Pro Ala Ser Ser Pro Gly Leu Asp Glu Ala Glu Phe Pro Pro Asp
            35                  40                  45

Ala Pro Val Leu Ser Asp Val Ser Gly His Arg Ala Gly Ser Ser Glu
50                  55                  60

Ala Ser Ala Arg Thr Ser Gly Pro Pro Ala Asp Asp His Leu Ser
65                  70                  75                  80

Leu Leu Arg Ala Ala Cys Glu Asp Gly Pro Leu Met Glu Ala Val Glu
                85                  90                  95
```

```
Leu Ala Ser Pro Ser Leu Ala Gly Leu Leu Ala Arg Val Ala Arg Gly
                100                 105                 110

Asp Thr Gly Gly Leu Lys Asp Lys Arg Leu Arg Arg Ala Ala Leu Ala
            115                 120                 125

Leu Leu Arg Tyr Asp Ile Arg Met Arg Thr Arg Pro Thr Pro Phe Gly
        130                 135                 140

Leu Phe Ala Gly Val Ser Gly Arg Phe Asp Thr Ser Ala Lys Trp
145                 150                 155                 160

Leu Ala Gly Thr Gly His Arg Thr Arg Thr Arg Ala Asp Met Glu Trp
                165                 170                 175

Leu Leu Ser Ala Val His Arg Leu Glu Arg Asp Arg Val Leu Leu Ala
            180                 185                 190

Gly Val Thr Val Gln Ala His Gln Thr Leu Thr Val Arg Gly Asp Arg
        195                 200                 205

Ile Val Leu Asp Cys Pro Ser Ala Leu Gly Lys Pro Leu Asn Gly Ser
    210                 215                 220

Thr Arg Ser Thr Val Ser Ala Arg Arg Ser Pro Val Val Ala Glu Ile
225                 230                 235                 240

Leu Gly Ala Ala Arg Arg Pro Val Leu Ala Gly Arg Leu Ala Gln Ser
                245                 250                 255

Val Ala Gln Arg Phe Glu Leu Pro Val Asp Arg Val Thr Gly Leu Leu
            260                 265                 270

Ala Asp Met Ala Ala Gln Glu Leu Leu Ile Thr Ala Leu Arg Pro Pro
        275                 280                 285

Leu Asp Gly Gly Asp Pro Leu Gln His Val Leu Asp Val Val Ala Thr
    290                 295                 300

Ala Glu Ala Arg Ala Gly Ser Pro Ala Glu Ala Met Ser Ser Asp Ser
305                 310                 315                 320

Ala Ala Leu Val Ala Ala Leu Arg Glu Val Asp Ala Arg Cys His Ala
                325                 330                 335

Tyr Asp Arg Thr Ala Val Gly Gln Gly Arg Arg Glu Leu Ala Glu Leu
            340                 345                 350

Ile Gln Ala Thr Arg Arg Val His Pro His Asp Thr Pro Leu His Val
        355                 360                 365

Asp Leu Arg Ile Asp Leu Glu Val Arg Leu Pro Glu Ile Val Arg Thr
    370                 375                 380

Glu Ile Glu Arg Ala Ala Glu Ala Leu Trp Arg Leu Ser Pro Pro Arg
385                 390                 395                 400

Arg Gly Met Arg Ala Leu Arg Arg Tyr His Glu Ala Phe Leu Glu Arg
                405                 410                 415

Tyr Gly Ala Asp Arg Ala Val Pro Leu Leu Glu Leu Leu Asp Asp Thr
            420                 425                 430

Arg Gly Leu Gly Pro Pro Ala Gly Tyr Lys Trp Pro Pro Ser Glu Thr
        435                 440                 445

Pro Ala Gly Pro Gln Glu Glu Pro Arg Arg Ser Ala Ala Leu Ala Arg
    450                 455                 460

Leu Val Ala Thr Ala Ala Arg His Gly Glu Arg Glu Ile Val Ile Asp
465                 470                 475                 480

Glu Glu Thr Ile Ala Glu Leu Val Tyr Asp Glu Ala Ala Pro Ala Asp
                485                 490                 495

Leu Pro Asn Ser Leu Glu Leu Gly Val His Val Val Ala Pro Ser Leu
            500                 505                 510

Asp Glu Leu Ser Ala Gly Thr Phe Arg Val Val Leu Ala Pro Gly Pro
        515                 520                 525
```

```
Gly Ser His His Ala Gly Ala Thr Leu Gly Arg Phe Thr Gly Leu Leu
        530                 535                 540

Pro Asp Val Asp Ala Glu Ser Ala Ala Arg Gln Ala Gly Arg Pro Leu
545                 550                 555                 560

His Ile Gln Asp Ala Val Ala Ala Asp Val Ala Phe Ile Pro Arg Ser
                565                 570                 575

Gly Arg Ala Ala Asn Leu Ala His Thr Pro Ser Tyr Ser Gly Arg Arg
            580                 585                 590

Ile Ser Val Gly Leu Pro Asp Ser Gly Arg Ala Gln Glu Leu Pro Leu
        595                 600                 605

Asp Glu Leu Gly Val Ala Ala Asn Leu Glu Arg Leu Cys Leu Val His
    610                 615                 620

Leu Pro Thr Gly Arg Glu Val Val Pro Ala Leu Pro Asn Met Val Ser
625                 630                 635                 640

Ala Phe Ala Gln Ala Pro Asn Pro Ala Arg Leu Leu Phe Glu Leu Gly
                645                 650                 655

Leu Glu Gly Gln Arg Leu Trp Glu Pro Trp Asp Trp Gly Ala Leu Ser
            660                 665                 670

Glu Met Pro Phe Leu Pro Gly Val Arg Tyr Gly Arg Thr Leu Leu Ala
        675                 680                 685

Ala Pro Ile Trp Arg Met Asp Gln Leu Arg Gly Pro Ala Ala Asp Ser
    690                 695                 700

Gly Pro Ala Ala Asp Trp Asp Ala Ala Leu Asp Arg Trp Arg Ala Glu
705                 710                 715                 720

Trp Asn Val Pro Arg Arg Val Leu Ala Val Ser Met Asp Gln Arg Leu
                725                 730                 735

Leu Leu Asp Leu Gly Asp Ala Trp His Arg Val Leu Leu Arg Asp Glu
            740                 745                 750

Leu Arg Arg Thr Pro Glu Leu Ile Ala Gln Gln Val Ala Gly Asp Glu
        755                 760                 765

Glu Gly Trp Leu Asp Arg Gly Asp Gly Gly Phe Pro Gly His Leu Ala
    770                 775                 780

Glu Ile Val Val Pro Leu Glu Arg Arg Asp Arg His Ala Ala Arg Pro
785                 790                 795                 800

Pro His Ile Arg Ala Thr Val Gly Gly Arg Glu Pro Thr Gly Ala Gly
                805                 810                 815

Gly Pro Trp Leu Tyr Leu Arg Leu Arg Val Pro Arg Arg Asn Gln Asp
            820                 825                 830

Asp Phe Leu Arg Asp Gln Val Pro Val Leu Val Arg Ala Gly Ile Gly
        835                 840                 845

His Gly Ala Asp Arg Trp Phe Phe Ile Arg Tyr Ser Asp Thr Ala Gly
    850                 855                 860

Gln His Leu Arg Val Arg Phe Arg Gly Glu Arg Glu Lys Leu Trp Ala
865                 870                 875                 880

Gly Leu Leu Pro Glu Ile Gly Ala Arg Leu Val Glu Trp Gln Arg Gln
                885                 890                 895

Gly Leu Leu Ala Gly His Glu Leu Gly Gln Tyr Asp Pro Glu Tyr Glu
            900                 905                 910

Arg Tyr Gly Gly Asp Ala Leu Ala Glu Phe Thr Glu Ala Ala Phe Gln
        915                 920                 925

His Asp Ser Ala Ala Ala Ile Ser Leu Leu Arg Leu Thr Arg Arg Ala
    930                 935                 940

Gly Phe Arg Tyr Thr Leu Asp Glu Val Thr Ala Ile Ser Ala Ala Ala
```

```
                945                 950                 955                 960
Leu Ala His Ala Phe Gly Pro Pro Ala Pro Val Val Glu Pro Val Pro
                965                 970                 975
Leu Val Gly Gly Leu Gln Trp Ala Pro Asp Leu Phe Asp Gly Asp Pro
                980                 985                 990
Ala Ala Ala Trp Met Ser Thr Thr Gly Ala Arg Arg Glu Leu Pro Pro
        995                1000                1005
Asp Tyr Arg Arg Glu Pro Ala Arg Trp Gln Lys Leu Ile Asp Pro
       1010                1015                1020
Thr Gly Gly Trp Arg Val Leu Arg Ala Asp Glu Asp Gly Cys Gln
       1025                1030                1035
Val Leu Ala Ala Leu Glu Ser Arg Asp Glu Ala Val Arg Arg Phe
       1040                1045                1050
Gly Thr Ala Phe Arg Glu Ala Ser Arg Pro Thr Asp Ser Pro Ser
       1055                1060                1065
Thr Gln Leu Arg Leu Val Gly Ser Leu Leu His Met Thr Cys Asn
       1070                1075                1080
Arg Leu Ile Gly Gly Ser Ala Glu Arg Glu Arg Ser Val Leu Gly
       1085                1090                1095
Leu Ala Arg Gly Ala Val Gln Asp Asn Leu Asn Arg Arg Arg His
       1100                1105                1110
Arg Ala
       1115

<210> SEQ ID NO 9
<211> LENGTH: 475
<212> TYPE: PRT
<213> ORGANISM: Microbispora sp. PTA-5024

<400> SEQUENCE: 9

Val Thr Pro Asp Arg His Pro Ala Arg Phe Leu Arg Gly Ser Ala Ala
 1                5                  10                 15

Arg Arg Ala Ala Arg Leu Val Arg Leu Val Ala Glu Arg Leu Ala Asp
                20                  25                 30

Pro Asp Glu Val Ala Gly Ile Ala Ala Arg Pro Gly Asn Ser Val Pro
            35                  40                  45

Ala Asn Gly Leu Ser Met Trp Ser Pro Ala Thr Leu Ser His Gly Phe
        50                  55                  60

Pro Gly Ile Ala Val Phe Tyr Ala Glu Leu Gly Arg Val Asp Pro Ala
65                  70                  75                  80

Trp Ser Ala Leu Ala His Arg His Leu Arg Ala Gly Ala Ala Val
                85                  90                  95

Glu Thr Ala Pro Ser Gly Gly Leu Phe Ala Gly Pro Ala Ser Leu Leu
            100                 105                 110

Ala Ala Ala Gln Ser Cys Ala Gly Pro Ala Gly His Tyr Arg Gly Leu
        115                 120                 125

Arg Arg Thr Leu Thr Ala Trp Leu Ala Ala Asp His Ala Gly Arg Leu
    130                 135                 140

Ala Ala Ala Arg Asp Arg Pro Gly Pro Gly Val Ala Trp Thr Asp Tyr
145                 150                 155                 160

Asp Val Val His Gly Leu Ser Gly Ser Thr Arg Leu Leu Leu Asp Ala
                165                 170                 175

Ala Arg Asp Pro Asp Asp Glu Thr Ala Ala Lys Ala Ser Gly Ala Val
            180                 185                 190

Thr Asp Thr Leu Arg His Leu Val Arg Leu Thr Glu Pro Ile Thr Val
```

```
            195                 200                 205
Asp Gly His Glu Val Pro Gly Trp Trp Val Pro Ser His Leu Gln Pro
210                 215                 220

Val Glu Gln Asp Arg Arg Asp Tyr Pro Arg Gly Asp Leu Asn Leu Gly
225                 230                 235                 240

Leu Ala His Gly Ala Ala Gly Pro Leu Ser Val Leu Ala Thr Ala Thr
                245                 250                 255

Leu His Gly Val Glu Val Pro Gly Gln Arg Glu Ala Val Ala Arg Leu
                260                 265                 270

Ala Glu Trp Leu Leu Gly Trp Thr Met Thr Asp Asp Thr Gly Ala Tyr
                275                 280                 285

Trp Pro Cys Arg Val Ser Trp Asp Glu Gln Ile Ala Ala Val Arg Pro
                290                 295                 300

Asp Thr Ser Phe Thr Arg Thr Ala Trp Cys Tyr Gly Ala Pro Gly Val
305                 310                 315                 320

Cys Ala Ala Leu His Arg Ala Gly Leu Ala Leu Gly Val Thr Glu Trp
                325                 330                 335

Arg Glu Val Ala Val Thr Ala Leu Leu Asp Gly Leu Arg Arg Asp Arg
                340                 345                 350

Ser Ala Trp Arg Val Asp Gly Ser Thr Val Cys His Gly Tyr Ala Gly
                355                 360                 365

Leu Leu Gln Val Leu Ser Arg Val Gly Ala Glu Ser Gly Asp Pro Arg
                370                 375                 380

Leu Leu Asp Gly Cys Leu Asp Val Ala Arg Met Val Leu Gly Glu Ala
385                 390                 395                 400

Asp Glu Ser Ala Pro Phe Val Phe Pro His Leu Val Pro Asp Ser Pro
                405                 410                 415

Asp Gly Trp Arg Asn Ala Thr Gly Tyr Leu Pro Leu Asp Gly Ala Gly
                420                 425                 430

Leu Leu Glu Gly Ala Ala Gly Val Ala Cys Ala Leu Leu Ser Val Ile
                435                 440                 445

Pro Pro Ser Ser Leu Gly Gly Thr Asp Pro Ala Pro Glu Arg Ala Asp
                450                 455                 460

Leu Pro Pro Trp Asp Arg Cys Leu Ala Leu Cys
465                 470                 475

<210> SEQ ID NO 10
<211> LENGTH: 215
<212> TYPE: PRT
<213> ORGANISM: Microbispora sp. PTA-5024

<400> SEQUENCE: 10

Met Thr Ala His Ser Asp Ala Gly Gly Val Pro Arg Pro Pro Glu Arg
1               5                   10                  15

Leu Leu Leu Gly Val Ser Gly Ser Val Ala Ala Leu Asn Leu Pro Ala
                20                  25                  30

Tyr Val Tyr Ala Phe Arg Ala Ala Gly Val Ala Arg Leu Ala Val Val
                35                  40                  45

Leu Thr Pro Ala Ala Glu Gly Phe Leu Pro Gly Ala Leu Arg Pro
                50                  55                  60

Ile Val Asp Ala Val His Thr Glu His Asp Gln Gly Lys Gly His Val
65                  70                  75                  80

Ala Leu Ser Arg Trp Ala Gln His Leu Val Leu Pro Ala Thr Ala
                85                  90                  95

Asn Leu Leu Gly Cys Ala Ala Ser Gly Leu Ala Pro Asn Phe Leu Ala
```

```
                  100                 105                 110
Thr Val Leu Leu Ala Ala Asp Cys Pro Ile Thr Phe Val Pro Ala Met
            115                 120                 125

Asn Pro Val Met Trp Arg Lys Pro Ala Val Arg Arg Asn Val Ala Thr
            130                 135                 140

Leu Arg Ala Asp Gly His Arg Val Val Asp Pro Leu Pro Gly Ala Val
145                 150                 155                 160

Tyr Glu Ala Ala Ser Arg Ser Ile Val Asp Gly Leu Thr Met Pro Arg
                165                 170                 175

Pro Glu Ala Leu Val Arg Leu Leu Gly Gly Gly Asp Asp Gly Ser Pro
            180                 185                 190

Ser Gly Gln Asp Gly Pro Val Gly Arg Ala Glu His Ala Glu His Ala
            195                 200                 205

Glu Ala Glu Ala Leu Ala
            210                 215

<210> SEQ ID NO 11
<211> LENGTH: 316
<212> TYPE: PRT
<213> ORGANISM: Microbispora sp. PTA-5024

<400> SEQUENCE: 11

Met Thr Val Pro Ala Phe Glu Leu Ser Asp Leu Thr Val Arg Tyr Gly
1               5                   10                  15

Pro Val Thr Ala Val Asp Gly Val Ser Ala Gly Ser Ala Pro Gly Leu
            20                  25                  30

Val Thr Ala Leu Leu Gly Pro Asn Gly Ala Gly Lys Ser Ser Leu Leu
        35                  40                  45

Arg Val Leu Ser Thr Val Ala Pro Pro Ser Ser Gly Thr Ala Arg Val
50                  55                  60

Phe Gly His Asp Thr Arg Ala Glu Pro Leu Ala Ala Arg Arg Arg Ile
65                  70                  75                  80

Gly Leu Val Phe Gln Glu Arg Ala Leu Asp Thr Asp Leu Ser Ala Glu
                85                  90                  95

Gln Asn Leu Arg Phe His Ala Arg Leu Phe Gly Val Gly Arg Ala Arg
            100                 105                 110

Ala Ala Glu Asp Ile Leu Val Leu Leu Glu Arg Phe Gly Leu Ala Gly
            115                 120                 125

Arg Gly Arg Asp Arg Val Glu Thr Leu Ser Gly Gly Leu Ala Arg Arg
            130                 135                 140

Leu Glu Ile Ala Arg Ala Leu Leu His Arg Pro Gly Leu Leu Ile Leu
145                 150                 155                 160

Asp Glu Pro Thr Asn Gly Leu Asp Pro Glu Ala Arg Gln Thr Val Trp
                165                 170                 175

Asp Asp Leu Ile Arg Leu Arg Ser Glu Leu Gly Val Thr Val Leu Tyr
            180                 185                 190

Ser Thr His Tyr Met Asp Glu Ala Glu Leu Ala Asp Gln Ile Ile Ile
            195                 200                 205

Leu Ser Glu Gly Arg Val Ala Gly Phe Gly Ser Pro Gly Arg Leu Lys
        210                 215                 220

Ser Glu Leu Arg Ser Ser Arg Ile Val Leu Val Thr His Asp Asp
225                 230                 235                 240

Thr Val Leu Ala Arg Leu Ala Glu Ala Gly Phe Asp Ala Val Ile Asp
                245                 250                 255

Ser Asp Gly Val Ala Val Arg Cys Arg Glu Pro Glu Ser Arg Met Ala
```

```
                260                 265                 270
Glu Val Ile Arg Ala Ala Gly Pro Leu Val Arg Ala Ser Val His
        275                 280                 285
His Pro Ser Met Asn Asp Val Phe Leu Ala His Thr Ala Ala Asn Arg
        290                 295                 300
Asp Arg Glu Ala Ala Asp Gly Thr Val Ser Cys Pro
305                 310                 315

<210> SEQ ID NO 12
<211> LENGTH: 242
<212> TYPE: PRT
<213> ORGANISM: Microbispora sp. PTA-5024

<400> SEQUENCE: 12

Val Ala His Arg Asp Val Leu Arg Gln Val Arg His Pro Gly Val Val
1               5                   10                  15

Val Ala Gln Ala Ala Gln Ile Val Phe Phe Val Leu Val Tyr Ala Val
                20                  25                  30

Gly Phe Arg Ser Met Ile Gly Ser Val Gly Gly Val Ser Phe Gly Ala
            35                  40                  45

Tyr Val Tyr Pro Gly Ile Ile Ala Ile Gln Val Val Met Leu Gly Val
        50                  55                  60

Gly Thr Gly Leu Thr Tyr Ala Met Asp Arg Glu Phe Gly Val Leu Arg
65                  70                  75                  80

Glu Met Gln Val Ala Pro Val Pro Arg Met Cys Leu Pro Leu Gly Lys
                85                  90                  95

Ile Leu Ala Ser Cys Val Leu Thr Ala Gln Ala Met Leu Met Leu
            100                 105                 110

Leu Pro Ala Pro Leu Leu Gly Leu Pro Leu Thr Pro Ala Arg Tyr Ala
        115                 120                 125

Ala Gly Ala Ala Val Tyr Leu Ala Thr Ala Ala Phe Ser Leu Ile
    130                 135                 140

Gly Leu Leu Leu Ala Val Ser Val Arg Arg Ile Glu Thr Leu Gln Ala
145                 150                 155                 160

Thr Val Gln Leu Ala Met Tyr Pro Leu Leu Phe Leu Ser Gly Ser Val
                165                 170                 175

Phe Lys Pro Asp Ala Val Pro Gly Trp Leu Ala Ala Leu Met Arg Leu
            180                 185                 190

Asn Pro Met Thr Tyr Ala Val Asp Leu Ala Arg His Val Leu Leu Pro
        195                 200                 205

Ser Ala Pro Gly Val Ser Tyr Leu Pro Val Trp Arg Asp Leu Leu Val
    210                 215                 220

Ile Ala Ala Leu Val Ala Ala Ala Ser Ala Ala Leu Arg Leu Arg Val
225                 230                 235                 240

Gly Arg

<210> SEQ ID NO 13
<211> LENGTH: 211
<212> TYPE: PRT
<213> ORGANISM: Microbispora sp. PTA-5024

<400> SEQUENCE: 13

Val Trp Leu Val Ala Leu Leu Ala Glu Gly Gly Arg Ser Val Glu Pro
1               5                   10                  15

Trp Pro Ala Val Ala Gln Arg Ile Ile Asp Ala Gly Cys Ala Glu Pro
                20                  25                  30
```

Ile Arg Pro Gly Arg Pro Thr Ala Ala Arg Leu Glu Ala Arg Tyr Val
         35                  40                  45

Phe Asp Leu Ala Gly Leu Arg His Gly Leu Pro Ala Met Gly Glu Leu
 50                  55                  60

Ala Gly Arg Thr Ala Leu Gly Pro Gly Ala Asp Pro Leu His Leu Thr
 65                  70                  75                  80

Asp Ala Asp Leu Tyr Val Ile Thr His Met Leu Phe Tyr Leu Thr Asp
                 85                  90                  95

Phe Gly Arg Arg Pro Phe Ser Ala Asp Glu Ala Glu Ser Arg Arg Val
                100                 105                 110

Arg Gly Leu Val Glu Val Leu Leu Gly Arg Gln Leu Ala Val Gly Asp
            115                 120                 125

Leu Asp Leu Ala Ala Glu Leu Leu Ala Cys Ala Gly Leu Thr Gly Ala
130                 135                 140

Asp Asp Arg Leu Ser Gly Cys Ala Trp Asn Arg Leu Ser Ala Ala Arg
145                 150                 155                 160

Arg Pro Asp Gly Ser Val Pro Ser Pro Leu Phe Arg Gln Ala Ala Leu
                165                 170                 175

Asp Arg Leu Ser Gly Glu Lys Ala Glu Ala Tyr Ala Phe Gly Thr Cys
            180                 185                 190

Tyr His Thr Thr Leu Ala Met Val Leu Ala Ala Thr Leu Thr Asp Gly
            195                 200                 205

Ala Asp Gly
210

<210> SEQ ID NO 14
<211> LENGTH: 249
<212> TYPE: PRT
<213> ORGANISM: Microbispora sp. PTA-5024

<400> SEQUENCE: 14

Met Ala Ala Leu Ile Ser Thr Glu Leu Leu Arg Leu Arg Ser Gly Phe
 1               5                  10                  15

Val Gly Trp Tyr Ile Leu Leu Ser Pro Ile Val Ile Ala Ile Pro Leu
             20                  25                  30

Tyr Leu Gly Ser Ile Phe Ser Pro Glu Gly Arg Ser Gly Arg Leu Trp
         35                  40                  45

Glu Thr Phe Ser Asn Val Thr Leu Glu Phe Trp Gly Val Leu Ile Pro
 50                  55                  60

Met Thr Ala Gly Leu Ile Ala Ala Leu Ala Val Arg Ala Asp Thr Glu
 65                  70                  75                  80

Pro Trp Arg Phe Leu Phe Ser Tyr Ala Ile Pro Arg Trp Arg Tyr Phe
                 85                  90                  95

Thr Ala Lys Val Ala Ala Leu Ala Val Ala Gln Leu Leu Ser Ala Thr
            100                 105                 110

Ile Leu Val Val Met Leu Ala Gly Gly Ala Leu Leu Thr Gly Gln Leu
            115                 120                 125

Ser Asn Ala Ala Ser Met Ile Leu Lys Val Ala Tyr Leu Pro Trp Ala
130                 135                 140

Ala Gly Leu Ala Ala Thr Ala Leu Ala Val Leu Val Cys Thr Val Trp
145                 150                 155                 160

Gly Leu Gly Pro Gly Ile Ala Leu Gly Val Ala Gly Met Met Ala Gly
                165                 170                 175

Ala Leu Ile Ser Asp Lys Ser Phe Trp Tyr Ala Ile Pro Pro Ala Trp
            180                 185                 190

```
Pro Met Arg Val Ile Leu Pro Leu Ala Asp Ile Arg Pro Asn Gly Leu
        195                 200                 205

Ala Leu Asp Ala Ser Ser Pro Leu His Asp Thr Ser Val Ile Pro Leu
    210                 215                 220

Ala Val Ala Leu Ser Ala Ala Ala Thr Ile Val Ile Leu Leu Ile Gly
225                 230                 235                 240

Gly Arg His Met Ala Arg Lys Glu Val
                245

<210> SEQ ID NO 15
<211> LENGTH: 236
<212> TYPE: PRT
<213> ORGANISM: Microbispora sp. PTA-5024

<400> SEQUENCE: 15

Met Ala Ala Leu Glu Ile Arg Asp Leu His Lys His Tyr Asp Asp Phe
1               5                   10                  15

His Ala Leu Asp Gly Ala Asn Leu Thr Val Pro Asp Gly Ser Leu Tyr
            20                  25                  30

Gly Leu Leu Gly Pro Asn Gly Ala Gly Lys Thr Thr Leu Met Lys Ala
        35                  40                  45

Val Thr Gly Leu Arg His Pro Thr Ser Gly His Ile Ser Leu Phe Gly
    50                  55                  60

Arg Pro Tyr Glu Arg Arg Leu Leu Thr Gln Val Gly Ala Leu Leu Glu
65                  70                  75                  80

Ser Pro Gly Leu Trp Thr Gln Leu Asp Ala Val Ser His Leu Arg Ile
                85                  90                  95

His Ala Arg Leu Arg Gly Val Pro Glu Thr Arg Ile Gly Glu Val Leu
            100                 105                 110

Ser Leu Met Asn Leu Thr Glu Val Ser Thr Arg Lys Val Ala Lys Tyr
        115                 120                 125

Ser Leu Gly Met Arg Trp Arg Leu Gly Ile Ala Ile Ala Leu Leu Gly
    130                 135                 140

Arg Pro Arg Leu Val Val Leu Asp Glu Pro Met Asn Gly Leu Asp Pro
145                 150                 155                 160

Val Gly Ile Arg Asp Met Arg Ala Thr Leu Arg Ala Leu Thr Ala Ala
                165                 170                 175

Gly Thr Thr Val Met Val Ser Ser His Gln Leu Ala Glu Ile Ala His
            180                 185                 190

Ile Cys Asp His Val Gly Val Leu Val Ala Gly Arg Thr Ala Tyr Glu
        195                 200                 205

Gly Pro Leu Pro Gly Leu Ala Val Asp Gly Asp Leu Glu Gln Gly Phe
    210                 215                 220

Phe Arg Leu Leu Glu Lys Ala Gly Ser Ala Val Arg
225                 230                 235

<210> SEQ ID NO 16
<211> LENGTH: 541
<212> TYPE: PRT
<213> ORGANISM: Microbispora sp. PTA-5024

<400> SEQUENCE: 16

Val Thr Glu Pro His Arg Leu Ile Ala Ser Asn Glu Arg Leu Gly Thr
1               5                   10                  15

Ala Pro Glu Ala Pro Ala Asp Asp Pro Gly Ala Ile Arg Thr Val
            20                  25                  30

Gly Val Ile Gly Gly Gly Thr Ala Gly Tyr Leu Thr Ala Leu Ala Leu
```

-continued

```
                35                  40                  45
Lys Ala Lys Arg Pro Trp Leu Asp Val Ala Leu Val Glu Ser Ala Asp
 50                  55                  60
Ile Pro Ile Ile Gly Val Gly Glu Ala Thr Val Ser Tyr Met Val Met
 65                  70                  75                  80
Phe Leu His His Tyr Leu Gly Ile Asp Pro Ala Glu Phe Tyr Gln His
                 85                  90                  95
Val Arg Pro Thr Trp Lys Leu Gly Ile Arg Phe Glu Trp Gly Ser Arg
                100                 105                 110
Pro Glu Gly Phe Val Ala Pro Phe Asp Trp Gly Thr Gly Ser Val Gly
                115                 120                 125
Leu Val Gly Ser Leu Arg Glu Thr Gly Asn Val Asn Glu Ala Thr Leu
                130                 135                 140
Gln Ala Met Leu Met Thr Glu Asp Arg Val Pro Val Tyr Arg Gly Glu
145                 150                 155                 160
Gly Gly His Val Ser Leu Met Lys Tyr Leu Pro Phe Ala Tyr His Met
                165                 170                 175
Asp Asn Ala Arg Leu Val Arg Tyr Leu Thr Glu Leu Ala Ala Arg Arg
                180                 185                 190
Gly Val Arg His Val Asp Ala Thr Val Ala Glu Val Arg Leu Asp Gly
                195                 200                 205
Pro Asp His Val Gly Gly Leu Ile Thr Thr Asp Gly Arg Leu His
                210                 215                 220
Tyr Asp Phe Tyr Val Asp Cys Thr Gly Phe Arg Ser Leu Leu Leu Glu
225                 230                 235                 240
Lys Ala Leu Gly Ile Pro Phe Glu Ser Tyr Ala Ser Ser Leu Phe Thr
                245                 250                 255
Asp Ala Ala Val Thr Gly Thr Leu Ala His Gly Gly His Leu Lys Pro
                260                 265                 270
Tyr Thr Thr Ala Thr Thr Met Asn Ala Gly Trp Cys Trp Thr Ile Pro
                275                 280                 285
Thr Pro Glu Ser Asp His Leu Gly Tyr Val Phe Ser Ser Ala Ala Ile
                290                 295                 300
Asp Pro Asp Asp Ala Ala Ala Glu Met Ala Arg Arg Phe Pro Gly Val
305                 310                 315                 320
Thr Arg Glu Ala Leu Val Arg Phe Arg Ser Gly Arg His Arg Glu Ala
                325                 330                 335
Trp Arg Gly Asn Val Met Ala Val Gly Asn Ser Tyr Ala Phe Val Glu
                340                 345                 350
Pro Leu Glu Ser Ser Gly Leu Leu Met Ile Ala Thr Ala Val Gln Ile
                355                 360                 365
Leu Val Ser Leu Leu Pro Ser Ser Arg Arg Asp Pro Leu Pro Ser Asp
                370                 375                 380
Ala Ala Asn Gln Ala Leu Ala His Arg Trp Asp Ala Ile Arg Trp Phe
385                 390                 395                 400
Leu Ser Ile His Tyr Arg Phe Asn Gly Arg Leu Asp Thr Pro Phe Trp
                405                 410                 415
Lys Glu Ala Arg Ala Glu Thr Asp Ile Ser Gly Ile Glu Pro Leu Leu
                420                 425                 430
Arg Leu Phe Ala Ala Gly Ala Pro Leu Thr Gly Arg Asp Ser Phe Thr
                435                 440                 445
Arg Tyr Leu Ala Asp Gly Ala Pro Leu Phe Tyr Gly Leu Glu Gly
                450                 455                 460
```

Val Asp Thr Leu Leu Leu Gly Gln Glu Val Pro Ala Arg Leu Leu Pro
465                 470                 475                 480

Pro Arg Glu Pro Pro Glu Gln Trp Arg Ala Arg Ala Ala Ala Ala Arg
            485                 490                 495

Ser Leu Ala Ser Arg Gly Leu Arg Gln Ser Glu Ala Leu Asp Ala Tyr
            500                 505                 510

Ala Ala Asp Pro Cys Leu Asn Ala Glu Leu Leu Ser Asp Ser Asp Ser
            515                 520                 525

Trp Ala Gly Glu Arg Val Ala Val Arg Ala Gly Leu Arg
530                 535                 540

<210> SEQ ID NO 17
<211> LENGTH: 178
<212> TYPE: PRT
<213> ORGANISM: Microbispora sp. PTA-5024

<400> SEQUENCE: 17

Met Thr Thr Gly Ala Thr Val Ala His Val Val Glu Pro Asp Gly Phe
1               5                   10                  15

Arg Ala Val Met Ala Thr Leu Pro Ala Ala Val Ala Ile Val Thr Ala
                20                  25                  30

Ala Ala Ala Asp Gly Arg Pro Trp Gly Met Thr Cys Ser Ser Val Cys
            35                  40                  45

Ser Val Thr Leu Thr Pro Pro Thr Leu Leu Val Cys Leu Arg Thr Ala
50                  55                  60

Ser Pro Thr Leu Ala Ala Val Val Ser Gly Arg Ala Phe Ser Val Asn
65                  70                  75                  80

Leu Leu Cys Ala Arg Ser Tyr Pro Val Ala Glu Leu Phe Ala Ser Ala
                85                  90                  95

Ala Ala Asp Arg Phe Asp Arg Val Arg Trp Arg Arg Pro Thr Gly Thr
            100                 105                 110

Gly Gly Pro His Leu Ala Asp Asp Ala Arg Ala Val Leu Asp Cys Arg
            115                 120                 125

Leu Ser Glu Ser Ala Glu Val Gly Asp His Met Val Val Phe Gly Glu
130                 135                 140

Val Arg Ala Ile Arg Arg Leu Ser Asp Glu Pro Pro Leu Met Tyr Gly
145                 150                 155                 160

Tyr Arg Arg Tyr Ala Pro Trp Pro Ala Asp Arg Gly Pro Gly Ala Val
                165                 170                 175

Gly Gly

<210> SEQ ID NO 18
<211> LENGTH: 430
<212> TYPE: PRT
<213> ORGANISM: Microbispora sp. PTA-5024

<400> SEQUENCE: 18

Val Asn Ala Glu Gln Leu Thr Gly Val Val Ile Ala Asp Leu Gly Val
1               5                   10                  15

Ile Val Val Val Ser Ala Leu Phe Gly Ala Leu Ala Arg Arg Cys Gly
                20                  25                  30

His Pro Thr Val Ile Gly Gln Ile Val Ala Gly Ile Ala Leu Gly Pro
            35                  40                  45

Thr Leu Leu Gly Arg Leu Pro Gly Asp Pro Ala Gly Trp Leu Phe Pro
50                  55                  60

```
Ala Gln Val Arg Pro Ser Leu Ser Val Leu Ser Gln Ile Ala Val Val
 65                  70                  75                  80

Ile Phe Met Phe Ala Val Gly Tyr Glu Val Asp Leu Arg Leu Leu Arg
                 85                  90                  95

Arg Gly Gly Arg Ser Ala Leu Cys Val Ala Ser Leu Ser Leu Ala Val
            100                 105                 110

Pro Met Thr Leu Gly Ala Ala Val Ala Val Leu Phe Arg Glu Val Phe
        115                 120                 125

Thr Val Gly Ser Pro Gly Gly Pro Gly Gly Pro Thr Phe Val Leu Phe
    130                 135                 140

Met Ala Val Ala Ile Ser Ile Thr Ala Leu Pro Val Leu Ala Ala Ile
145                 150                 155                 160

Val Arg Glu Arg Gly Leu Ala Gly Thr Ala Ala Gly Thr Val Ala Thr
                165                 170                 175

Ala Ala Ala Gly Leu Met Asp Val Ala Ala Trp Thr Thr Leu Ala Ala
            180                 185                 190

Val Leu Ala Glu Thr Gly Asp Ala Asp Glu Pro Thr Val Ser His Val
        195                 200                 205

Pro Trp Met Leu Ala Leu Pro Ala Leu Thr Ala Phe Ala Val Ala Met
    210                 215                 220

Phe Leu Val Val Arg Pro Leu Leu Gly Trp Leu Thr Arg Arg Pro Gly
225                 230                 235                 240

Ala Met Trp Gly Arg Leu Pro Ala Ala Phe Ala Leu Ala Leu Gly Ser
                245                 250                 255

Ala Trp Gly Thr Ala Ala Leu Gly Leu His Pro Val Phe Gly Gly Leu
            260                 265                 270

Leu Ala Gly Leu Val Met Pro Arg Arg Asp Gly Ala Pro Glu Pro Glu
        275                 280                 285

Val Leu Arg Pro Met Glu Gln Thr Ala Glu Leu Leu Pro Leu Phe
        290                 295                 300

Phe Val Met Thr Gly Leu Ser Ala Asp Ile Ser Ala Ile Glu Pro Gly
305                 310                 315                 320

Gly Leu Ile Leu Leu Ala Val Leu Leu Val Ala Ala Ile Gly Gly Lys
                325                 330                 335

Leu Val Pro Ala Tyr Ala Ala Ser Arg Leu Thr Gly Leu Asp Ser Gly
            340                 345                 350

Glu Ser Ala Val Val Ala Val Leu Val Asn Thr Arg Gly Leu Thr Glu
        355                 360                 365

Leu Ile Val Leu Asp Val Gly Leu Ser Ala His Val Ile Asp Glu Arg
    370                 375                 380

Leu Phe Thr Val Leu Val Val Met Ala Leu Ile Thr Thr Ala Met Thr
385                 390                 395                 400

Ala Pro Leu Leu Thr Ala Leu Arg Arg Glu Glu Arg Arg Gly
                405                 410                 415

Arg Gln Ala Ala Pro Leu Ser Arg Ala Thr Ala Trp Arg Met
            420                 425                 430

<210> SEQ ID NO 19
<211> LENGTH: 68
<212> TYPE: PRT
<213> ORGANISM: artificial sequence
<220> FEATURE:
<223> OTHER INFORMATION: synthetic primer
```

-continued

<400> SEQUENCE: 19

Gly Thr Ser Ala Cys Ser Trp Ser Ser Thr Gly Gly Trp Ser Ser Tyr
1               5                   10                  15

Thr Ser Trp Ser Ser Ala Cys Ser Gly Gly Ser Cys Cys Ser Thr Gly
                20                  25                  30

Cys Ala Cys Ser Trp Ser Ser Cys Cys Ser Gly Gly Ser Gly Gly Ser
            35                  40                  45

Trp Ser Ser Ala Ala Cys Trp Ser Ser Trp Ser Ser Thr Cys Cys Trp
    50                  55                  60

Ser Ser Thr Gly
65

<210> SEQ ID NO 20
<211> LENGTH: 27
<212> TYPE: DNA
<213> ORGANISM: artificial sequence
<220> FEATURE:
<223> OTHER INFORMATION: synthetic primer

<400> SEQUENCE: 20
aagcttgcat ctgcgtgggc gtcctgc                                    27

<210> SEQ ID NO 21
<211> LENGTH: 29
<212> TYPE: DNA
<213> ORGANISM: artificial sequence
<220> FEATURE:
<223> OTHER INFORMATION: synthetic primer

<400> SEQUENCE: 21
tctagacggt ccgaagatca tggccgcgg                                  29

<210> SEQ ID NO 22
<211> LENGTH: 30
<212> TYPE: DNA
<213> ORGANISM: artificial sequence
<220> FEATURE:
<223> OTHER INFORMATION: synthetic primer

<400> SEQUENCE: 22
tctagatcca tgtgaaccgg cgggtggccg                                 30

<210> SEQ ID NO 23
<211> LENGTH: 30
<212> TYPE: DNA
<213> ORGANISM: artificial sequence
<220> FEATURE:
<223> OTHER INFORMATION: synthetic primer

<400> SEQUENCE: 23
gaattccggt cgctctcctc gtcctttgcc                                 30

<210> SEQ ID NO 24
<211> LENGTH: 19
<212> TYPE: DNA
<213> ORGANISM: artificial sequence
<220> FEATURE:
<223> OTHER INFORMATION: synthetic primer

<400> SEQUENCE: 24
cgcgctgctc ggggccaac                                             19

```
<210> SEQ ID NO 25
<211> LENGTH: 20
<212> TYPE: DNA
<213> ORGANISM: artificial sequence
<220> FEATURE:
<223> OTHER INFORMATION: synthetic primer

<400> SEQUENCE: 25
aggaaacggc cagcccgtgg                                          20

<210> SEQ ID NO 26
<211> LENGTH: 31
<212> TYPE: DNA
<213> ORGANISM: artificial sequence
<220> FEATURE:
<223> OTHER INFORMATION: synthetic primer

<400> SEQUENCE: 26
tttttcatat gggtgggagt gatcggcggc g                             31

<210> SEQ ID NO 27
<211> LENGTH: 35
<212> TYPE: DNA
<213> ORGANISM: artificial sequence
<220> FEATURE:
<223> OTHER INFORMATION: synthetic primer

<400> SEQUENCE: 27
tttttgtcga cctactgctg gccgcggtcc ggact                         35

<210> SEQ ID NO 28
<211> LENGTH: 20
<212> TYPE: DNA
<213> ORGANISM: artificial sequence
<220> FEATURE:
<223> OTHER INFORMATION: synthetic primer

<400> SEQUENCE: 28
gcagccaggc tcgcaccggc                                          20

<210> SEQ ID NO 29
<211> LENGTH: 16
<212> TYPE: DNA
<213> ORGANISM: artificial sequence
<220> FEATURE:
<223> OTHER INFORMATION: synthetic primer

<400> SEQUENCE: 29
cgcccgtaac gagcga                                              16

<210> SEQ ID NO 30
<211> LENGTH: 17
<212> TYPE: DNA
<213> ORGANISM: artificial sequence
<220> FEATURE:
<223> OTHER INFORMATION: synthetic primer

<400> SEQUENCE: 30
gcagcttctg ctgctga                                             17

<210> SEQ ID NO 31
<211> LENGTH: 16
<212> TYPE: DNA
<213> ORGANISM: artificial sequencer
<220> FEATURE:
<223> OTHER INFORMATION: synthetic primer
```

```
<400> SEQUENCE: 31
tcccggccag ccactt                                              16

<210> SEQ ID NO 32
<211> LENGTH: 21
<212> TYPE: DNA
<213> ORGANISM: artificial sequence
<220> FEATURE:
<223> OTHER INFORMATION: synthetic primer

<400> SEQUENCE: 32
ccggaaagga gcgagcatat g                                        21

<210> SEQ ID NO 33
<211> LENGTH: 18
<212> TYPE: DNA
<213> ORGANISM: artificial sequence
<220> FEATURE:
<223> OTHER INFORMATION: synthetic primer

<400> SEQUENCE: 33
cagatctgcc aatacagt                                            18

<210> SEQ ID NO 34
<211> LENGTH: 112
<212> TYPE: DNA
<213> ORGANISM: artificial sequence
<220> FEATURE:
<223> OTHER INFORMATION: synthetic primer
<220> FEATURE:
<221> NAME/KEY: misc_feature
<222> LOCATION: (32)..(37)
<223> OTHER INFORMATION: n is a, c, g, or t
<220> FEATURE:
<221> NAME/KEY: misc_feature
<222> LOCATION: (41)..(49)
<223> OTHER INFORMATION: n is a, c, g, or t
<220> FEATURE:
<221> NAME/KEY: misc_feature
<222> LOCATION: (56)..(61)
<223> OTHER INFORMATION: n is a, c, g, or t
<220> FEATURE:
<221> NAME/KEY: misc_feature
<222> LOCATION: (65)..(67)
<223> OTHER INFORMATION: n is a, c, g, or t
<220> FEATURE:
<221> NAME/KEY: misc_feature
<222> LOCATION: (71)..(82)
<223> OTHER INFORMATION: n is a, c, g, or t
<220> FEATURE:
<221> NAME/KEY: misc_feature
<222> LOCATION: (86)..(88)
<223> OTHER INFORMATION: n is a, c, g, or t
<220> FEATURE:
<221> NAME/KEY: misc_feature
<222> LOCATION: (95)..(97)
<223> OTHER INFORMATION: n is a, c, g, or t

<400> SEQUENCE: 34
cggtgtcgag gagatcaccg ccgggccggc gnnnnnagc nnnnnnnnnt gcaccnnnn    60 ntgcnnnagc nnnnnnnnnn nnagcnnntg cagcnnntgc tgctgaagat ct         112

<210> SEQ ID NO 35
<211> LENGTH: 112
<212> TYPE: DNA
<213> ORGANISM: artificial sequence
<220> FEATURE:
<223> OTHER INFORMATION: synthetic primer
```

```
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (26)..(37)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t
<220> FEATURE:
<221> NAME/KEY: misc_feature
<222> LOCATION: (47)..(52)
<223> OTHER INFORMATION: n is a, c, g, or t
<220> FEATURE:
<221> NAME/KEY: misc_feature
<222> LOCATION: (59)..(67)
<223> OTHER INFORMATION: n is a, c, g, or t
<220> FEATURE:
<221> NAME/KEY: misc_feature
<222> LOCATION: (71)..(76)
<223> OTHER INFORMATION: n is a, c, g, or t

<400> SEQUENCE: 35
ttcagcagca nnngctgcan nngctnnnnn nnnnnnnnct nnngcannnn nnggtgcann      60 nnnnnnnngct nnnnnncgcc ggcccggcgg tgatctcctc gacaccgatc ga            112

<210> SEQ ID NO 36
<211> LENGTH: 171
<212> TYPE: DNA
<213> ORGANISM: artificial sequence
<220> FEATURE:
<223> OTHER INFORMATION: synthetic primer
<220> FEATURE:
<221> NAME/KEY: misc_feature
<222> LOCATION: (100)..(105)
<223> OTHER INFORMATION: n is a, c, g, or t
<220> FEATURE:
<221> NAME/KEY: misc_feature
<222> LOCATION: (109)..(117)
<223> OTHER INFORMATION: n is a, c, g, or t
<220> FEATURE:
<221> NAME/KEY: misc_feature
<222> LOCATION: (124)..(129)
<223> OTHER INFORMATION: n is a, c, g, or t
<220> FEATURE:
<221> NAME/KEY: misc_feature
<222> LOCATION: (133)..(135)
<223> OTHER INFORMATION: n is a, c, g, or t
<220> FEATURE:
<221> NAME/KEY: misc_feature
<222> LOCATION: (139)..(150)
<223> OTHER INFORMATION: n is a, c, g, or t
<220> FEATURE:
<221> NAME/KEY: misc_feature
<222> LOCATION: (154)..(156)
<223> OTHER INFORMATION: n is a, c, g, or t
<220> FEATURE:
<221> NAME/KEY: misc_feature
<222> LOCATION: (163)..(165)
<223> OTHER INFORMATION: n is a, c, g, or t

<400> SEQUENCE: 36
atgcccgctg acatcctgga gacccggact tccgagaccg aggacctgct cgacctcgac      60
ctctcgatcg gtgtcgagga gatcaccgcc gggccggcgn nnnnnagcnn nnnnnnntgc     120
accnnnnnnt gcnnnagcnn nnnnnnnnnn agcnnntgca gcnnntgctg c              171
```